United States Patent [19]
Osborn, III et al.

[11] Patent Number: 5,688,259
[45] Date of Patent: Nov. 18, 1997

[54] ABSORBENT ARTICLE HAVING RESILIENT CENTER

[75] Inventors: Thomas W. Osborn, III; Theresa L. Johnson; Letha M. Hines; Robb E. Olsen, all of Cincinnati, Ohio

[73] Assignee: The Procter & Gamble Company, Cincinnati, Ohio

[21] Appl. No.: 596,061

[22] Filed: Feb. 6, 1996

Related U.S. Application Data

[63] Continuation of Ser. No. 238,191, May 4, 1994, abandoned, which is a continuation of Ser. No. 915,202, Jul. 23, 1992, abandoned.

[51] Int. Cl.$^6$ ............................. A61F 13/15; A61F 13/20
[52] U.S. Cl. ..................... 604/385.1; 604/378; 604/380
[58] Field of Search ........................... 604/358, 378, 604/379, 380, 383, 385.1

[56] References Cited

U.S. PATENT DOCUMENTS

| | | |
|---|---|---|
| 2,064,431 | 12/1936 | Jurgensen . |
| 4,828,555 | 5/1989 | Hermansson . |
| 4,917,697 | 4/1990 | Osborn, III et al. ............ 604/387 |
| 5,009,653 | 4/1991 | Osborn, III ..................... 604/378 |
| 5,181,563 | 1/1993 | Amaral . |
| 5,197,959 | 3/1993 | Buell . |
| 5,211,641 | 5/1993 | Roos et al. . |

FOREIGN PATENT DOCUMENTS

| | | |
|---|---|---|
| 0 668 066A2 | 8/1995 | European Pat. Off. . |
| 2 191 098 | 12/1987 | United Kingdom . |
| WO 91/03999 | 4/1991 | WIPO . |
| WO 93/01779 | 2/1993 | WIPO . |
| WO 93/01780 | 2/1993 | WIPO . |
| WO 93/01781 | 2/1993 | WIPO . |
| WO 93/01782 | 2/1993 | WIPO . |
| WO 93/01783 | 2/1993 | WIPO . |
| WO 93/01784 | 2/1993 | WIPO . |
| WO 93/02235 | 2/1993 | WIPO . |
| WO 93/02251 | 2/1993 | WIPO . |

*Primary Examiner*—P. Zuttarelli
*Attorney, Agent, or Firm*—Jeffrey V. Bamber; Steven W. Miller; Jacobus C. Rasser

[57] ABSTRACT

An absorbent article, such as a sanitary napkin is provided. The sanitary napkin of the present invention has a body-conforming configuration that is provided at least in part by a longitudinally-oriented resilient hump-forming element. The hump-forming element is positioned to form a hump along the longitudinal centerline on the body surface of the sanitary napkin. The sanitary napkin may also be provided with bending axes. The sanitary napkin may also be provided in a curved configuration.

11 Claims, 11 Drawing Sheets

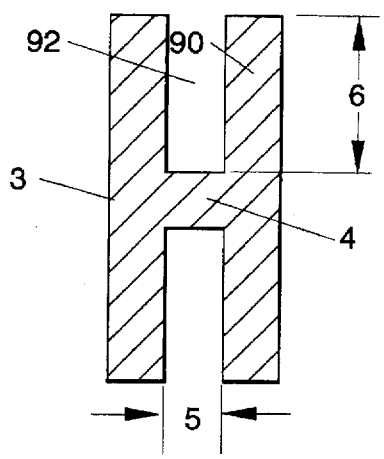
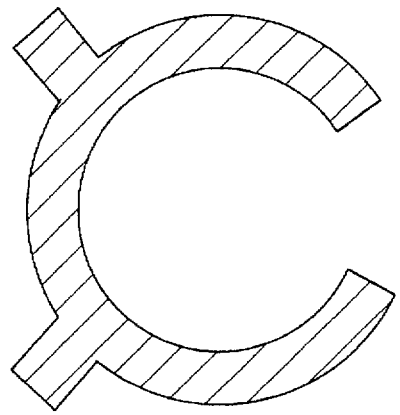
Fig. 8          Fig. 11
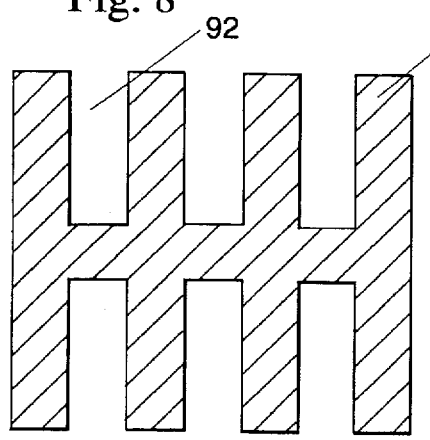
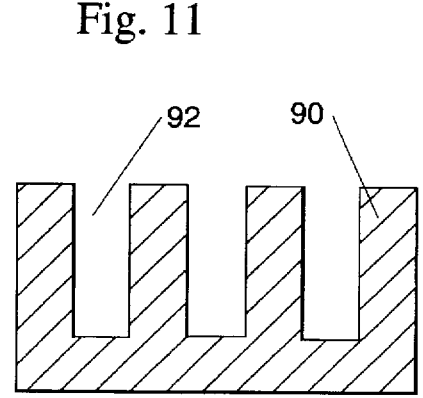
Fig. 9          Fig. 10
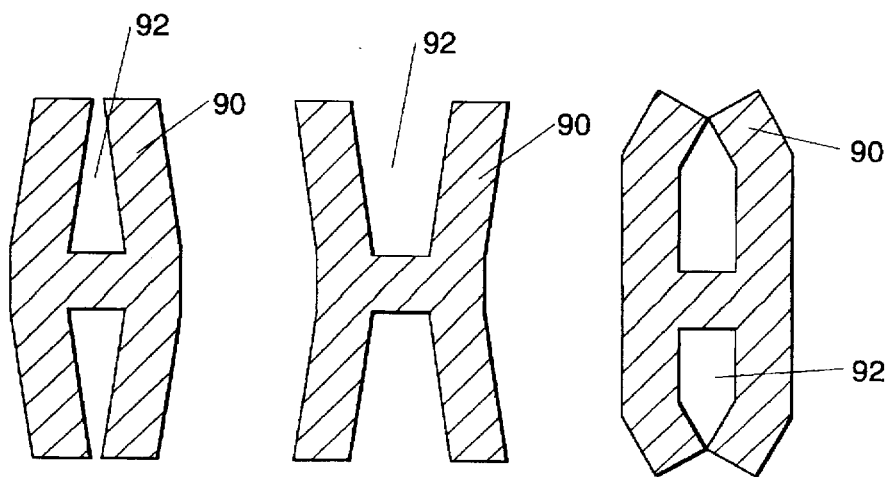
Fig. 11A          Fig. 11B          Fig. 11C

ABSORBENT ARTICLE HAVING RESILIENT CENTER

This is a continuation of application Ser. No. 08/238,191, filed on May 4, 1994, now abandoned which was a continuation of application Ser. No. 07/915,202, filed Jul. 23, 1992, now abandoned.

FIELD OF THE INVENTION

The present invention relates to absorbent articles, especially catamenial articles such as sanitary napkins. Such articles are especially adapted for absorbing various body fluids, especially menses, while providing comfort and fit to the wearer.

BACKGROUND OF THE INVENTION

A wide variety of structures for disposable absorbent articles to collect body fluids are known in the art. Commercial absorbent articles include diapers, adult incontinence products, catamenials and bandages. Disposable products of this type comprise some functional members for receiving, absorbing and retaining fluids. Generally, such absorbent articles contain a core of absorbent materials mainly comprising fibrous cellulose. Typically, such articles include a fluid-permeable topsheet, an absorbent core and a fluid-impermeable backsheet.

In the case of catamenial pads, women have come to expect a high level of performance in terms of comfort and fit, retention of fluid, and minimal staining. Above all, leakage of fluid from the pad onto undergarments is regarded as totally unacceptable.

Improving the performance of sanitary napkins continues to be a formidable undertaking, although a number of improvements have been made in both their materials and structures. However, eliminating leakage, particularly along the inside of the thighs, without compromising fit and comfort, has not met the desired needs of the consumer.

Leakage from sanitary napkins is generally attributed to a high concentration of fluid at the point where the menses exits the body and immediately contacts the surface of the napkin. At this point of deposit, the napkins absorbent material quickly becomes super-saturated. The blood migrates radially from this point and leaks from the sides nearest the wearer's legs. This often results in the smearing of blood on the body and soiling of the undergarments. Attempts to eliminate leakage include: construction of a densified edge to hold the fluid back (U.S. Pat. No. 4,820, 295, Chapas et al, issued Apr. 11, 1989); barrier sheets surrounding the article (U.S. Pat. No. 4,666,439, Williams et al, issued May 19, 1987); and "winged" side edges which wrap around the panties, and providing sanitary napkins with elasticized longitudinal side edges.

Sanitary napkins provided with wings of various types (not all of which do not wrap around the wearer's panties, or control side leakage, however) are described in Japanese patent publications 40-36391, 46-12554, and 50-100399, and in U.S. Pat. No. 4,285,343 issued to McNair on Aug. 25, 1981, U.S. Pat. No. 4,589,876 issued May 20, 1986 to Van Tilburg, U.S. Pat. No. 4,608,047 issued to Mattingly on Aug. 26, 1986, and U.S. Pat. No. 4,687,478 issued Aug. 18, 1987 to Van Tilburg.

Sanitary napkins provided with elastics of various types are disclosed in European Patent Application Publication No. 0 091 412 A2 published Oct. 12, 1983, P&G UK Patent Application 2 168 253 A published Jun. 18, 1986 (which also discloses means for holding the side flaps therein in an upwardly folded configuration other than elastics), and U.S. Pat. No. 4,701,177 issued to Ellis, et al. on Oct. 20, 1987, U.S. Pat. No. 4,758,241 issued to Papajohn on Jul. 19, 1988, U.S. Pat. No. 4,770,657 issued to Ellis, et al. on Sept. 13, 1988, U.S. Pat. No. 4,944,735 issued to Mokry on Jul. 31, 1990, and U.S. Pat. No. 5,032,121 issued to Mokry on Jul. 16, 1991. The disclosures of all these documents are incorporated by reference herein.

Unfortunately, overdensifying sections of the sanitary napkins detracts from comfort, in-use. Some users are not attracted to the "winged" product, and others are not satisfied with the barrier product.

There are also a number of problems with using elastics for the above purposes. The addition of elastics increases the cost of producing sanitary napkins. The attachment of elastic strands to a moving web during the manufacturing of sanitary napkins is a fairly complicated and expensive process. The use of elastics also creates wrinkles along the upper parts of the sanitary napkin. Another problem is that the use of elastics for the purpose of causing a sanitary napkin to assume a curved shape is dependent on the thickness of the sanitary napkin. It is more difficult to achieve curvature in sanitary napkins having relatively thick absorbent means using elastics. Using elastics in thick products creates stresses in the elastics which resist the effort to impart curvature to the sanitary napkin. These stresses also tend to cause the elastics to lose their modulus of elasticity. The use of elastics also adds significant thickness to the product's longitudinal side barriers. This often results in a sanitary napkin that is less comfortable for the wearer.

Thus, the search for improved ways of reducing leakage from the longitudinal side edges of sanitary napkins has continued.

Further, since a large part of most absorbent articles remains relatively dry and not utilized, the search for improved ways of directing fluids from the point of deposit to the areas of the article not fully utilized to avoid supersaturation and reduce or eliminate leakage has also continued.

Apart from undergarment soiling, the user of modern sanitary napkins, and the like, has come to expect that the surface of such articles will provide a cleaner, more sanitary and drier aspect than common cloth or nonwoven materials have historically provided. Thus, modern sanitary napkins, diapers and incontinence devices are typically provided with topsheets that are designed to move fluids rapidly through said topsheets and into an underlying absorbent core for storage. As can be envisaged, the more rapid and thorough this movement, the drier and cleaner the surface of the article.

Several references that describe the use of fibers with particular cross-sections having channels or grooves therein are described in EPO Application 391,814, Phillips et al, published Oct. 10, 1990, U.S. Pat. No. 4,723,954, Pieniak, Feb. 9, 1988, U.S. Pat. No. 4,798,603, Meyer et al, Jan. 17, 1989, U.S. Pat. No. 4,973,325, Sherrod et al, Nov. 27, 1990, EPO Application 397,110, Latimer et al, filed Aug. 5, 1990, French Patent 955,625, published by Paul Chevalier on Jan. 16, 1950, U.S. Pat. No. 3,121,040, issued to Shaw on Feb. 11, 1964, U.S. Pat. No. 4,054,709, issued to Belitsin, et al. on Oct. 18, 1977, See also U.S. Pat. No. 4,179,259, Belitsin, which includes some curling disclosure, U.S. Pat. No. 4,381, 325, issued to Masuda, et al., on Apr. 26, 1983, European Patent Application 88306987.4, publication number 0,301, 874, published Feb. 1, 1989, Wilkes, et al., U.S. Pat. No.

4,286,005, issued to Berger on Aug. 25, 1981, U.S. Pat. No. 4,623,329, issued to Drobish, et al., on Nov. 18, 1986, Japanese Patent Application 151617-1979, published Nov. 29, 1979, Teijin KK, U.S. Pat. Nos. 4,842,792, issued Jun. 27, 1989, and 4,954,398, Sept. 4, 1990, both to Bagrodia et al., U.S. Pat. No. 4,868,031, Modrak et al, issued Sept. 19, 1989.

The present invention is intended not only to provide a curved, body-conforming sanitary napkin with the desired, directional movement of fluids noted above, which allows improved use of the overall absorbent capacity of the article and less side-leakage, but also is also intended to provide a means to draw fluids through the topsheet, thereby enhancing the desired dry, sanitary benefits, in-use.

Furthermore, the articles which employ the technology embodied in the present invention are intended to be more comfortable and better fitting than articles which rely, for example, on highly dense absorbent core regions to achieve fluid movement. Stated otherwise, the technology herein is intended to achieve the fluid directionality and handling characteristics available from dense, but uncomfortable, cores in a soft, pliable, low-density and comfortable pad.

It is, therefore, an object of the present invention to provide disposable absorbent articles having improved fluid absorption and retention. It is a further object herein to provide such articles with improved fluid transport away from the skin. It is a particular object herein to provide sanitary napkins and pantiliners with attributes including, but not limited to, improved softness and flexibility, improved fit and improved stain reduction.

These advantages are obtained herein, as will be seen from the following disclosure.

SUMMARY OF THE INVENTION

The present invention provides a body-conforming absorbent article, such as a sanitary napkin. The sanitary napkin of the present invention has a longitudinally-oriented resilient hump-forming element positioned to form a hump along the longitudinal centerline on the body surface of the sanitary napkin.

A preferred embodiment of the sanitary napkin of the present invention comprises a liquid pervious topsheet, a liquid impervious backsheet, and an absorbent core. The absorbent core is positioned between the topsheet and backsheet. The topsheet and backsheet are joined together around the periphery of the sanitary napkin. The sanitary napkin also comprises a fastener for attaching the sanitary napkin to the crotch region of the wearer's panties.

The hump-forming element has an uncompressed configuration and a compressed configuration. The hump-forming element assumes its compressed configuration when subjected to laterally inwardly-oriented forces. The hump-forming element comprises an upper portion that is nearer the body surface of said absorbent article than the other portions of the hump-forming element, and longitudinal sides. When the sanitary napkin is subjected to laterally inwardly-oriented compressive forces, the longitudinal sides of the hump-forming element move laterally inward toward each other and the upper portion of the hump-forming element rises upward in a direction away from the garment surface to come in closer contact with the wearer's body.

The hump-forming element is preferably resilient in response to laterally inwardly-oriented forces. The hump-forming element tends to return toward its uncompressed configuration when the laterally-inward compressive forces are removed. The hump-forming element is also resilient in response to forces exerted on the body surface of the sanitary napkin in a direction toward the garment surface.

The hump-forming element provides a hump on the body surface in the central region of the sanitary napkin. The hump has a base with longitudinal side portions and transverse end portions. The sanitary napkin has longitudinal side regions outboard of the base of the hump. The longitudinal side regions are preferably more flexible than said central region of the sanitary napkin. The sanitary napkin is preferably provided with at least one bending axis in each of the longitudinal side regions laterally outboard of the longitudinal side portions of the base of the hump. Parts of the longitudinal side regions are located laterally inboard of the bending axes on each side of the hump, and parts are located laterally outboard of the bending axes.

Preferably, at least a portion of those parts of each of said longitudinal side regions located laterally outboard of the bending axes are predisposed to bend upward when the sanitary napkin is subjected to laterally inwardly-oriented compressive forces. The portions of said longitudinal side regions located laterally outboard of said bending axes are capable of returning toward their uncompressed positions when laterally inwardly-oriented compressive forces are removed from the absorbent article.

In addition, the end regions of the sanitary napkin are preferably more flexible than the central region. This may allow the end regions to bend about (generally transversely oriented) hump/end region axes located at, or longitudinally outboard of, the transverse end portions of the base of the hump.

Further, the fastener for attaching the sanitary napkin to the wearer's undergarment may be located only in the end regions so that the garment surface of the central region of the sanitary napkin is capable of separating from the wearer's undergarments for improved contact of the central region with the wearer's body while the end regions of the sanitary napkin remain attached to the wearer's undergarments.

DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 8 is a cross-sectional view of a symmetrical "H" shaped capillary channel fiber with a planar base (4), width-between walls (5), and depth-of-walls (6).

FIG. 9 is a cross-sectional view of a capillary channel fiber having a "multiple H" shaped configuration.

FIG. 10 is a cross-sectional view of a "multiple U" shaped capillary channel fiber.

FIG. 11 is a cross-sectional view of a modified "C" shaped capillary channel fiber.

FIG. 11A is a cross-sectional view of an H-shaped capillary channel fiber in a partially collapsed state. (While not optimal, such fibers can be used herein.)

FIG. 11B is a cross-sectional view of an expanded capillary channel fiber.

FIG. 11C is a cross-sectional view of a wholly collapsed capillary channel fiber. (Such fibers are preferably not used herein.)

DETAILED DESCRIPTION OF THE INVENTION

1. General Characteristics of the Absorbent Article

Figure 1:
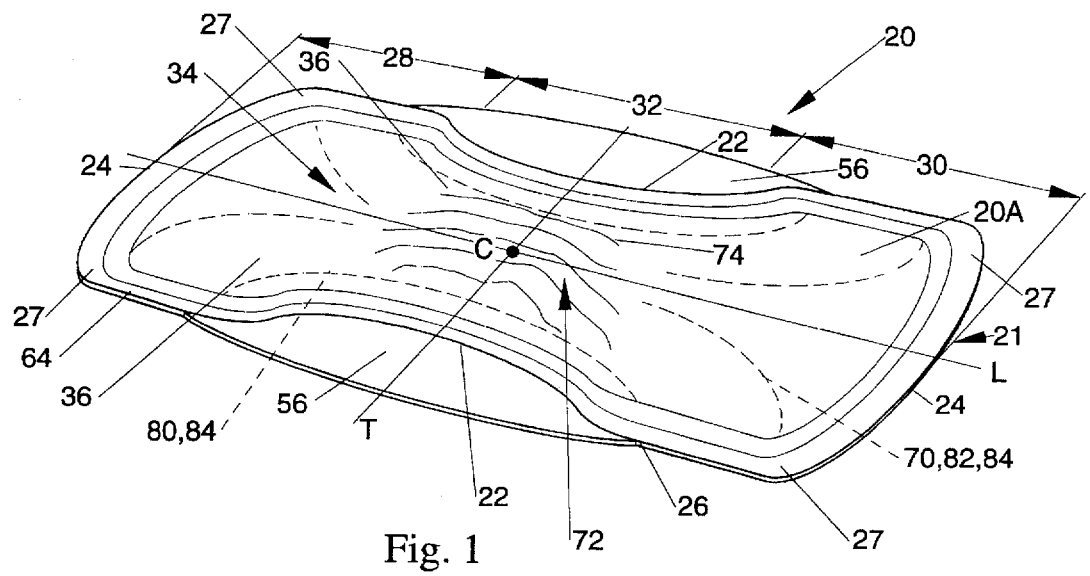
FIG. 1 is a perspective view of a preferred sanitary napkin according to the present invention.

A preferred embodiment of a unitary disposable absorbent article of the present invention is the catamenial pad, sanitary napkin 20, shown in FIG. 1.

The term "absorbent article", as used herein, refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity.

The term "sanitary napkin", as used herein, refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the body of the wearer while the garment surface 20B is on the opposite side and is intended to be placed adjacent to the wearer's undergarments when the sanitary napkin 20 is worn.

The sanitary napkin 20 has two centerlines, a longitudinal centerline, L, and a transverse centerline, T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 also shows that the sanitary napkin 20 has a periphery 26 which is defined by the outer edges of the sanitary napkin 20 in which the longitudinal edges (or "side edges") are designated 22 and the end edges (or "ends") are designated 24, and the corners of the sanitary napkin are designated 27.

The sanitary napkin has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the sanitary napkin. A detailed description of the central region 32 and the two end regions 28 and 30 is contained in U.S. Pat. No. 4,690,680 issued to Higgins on Sept. 1, 1987.

The sanitary napkin also has a longitudinally-oriented (or longitudinal) central region 34 disposed along the length of at least a portion of the longitudinal centerline L, and longitudinal side regions 36 laterally outboard of the longitudinal central region 34. The individual components of the sanitary napkin (described below) may have portions that coincide with the regions described in this and the foregoing paragraph.

Figure 2:
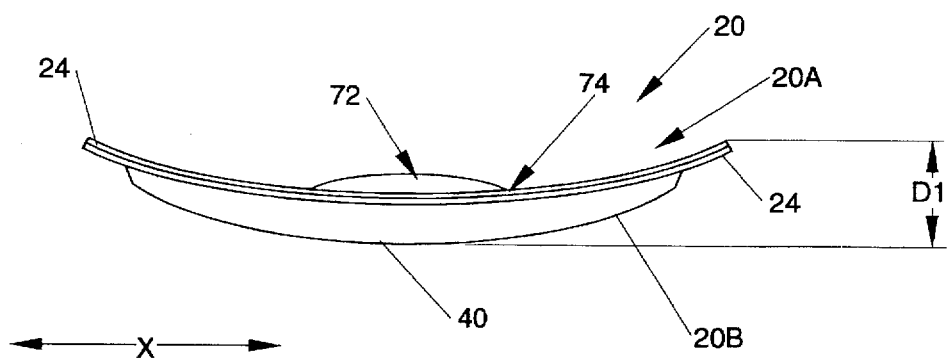
FIG. 2 is a schematic longitudinal side view of the sanitary napkin shown in FIG. 1 (shown without flaps).
Figure 3:
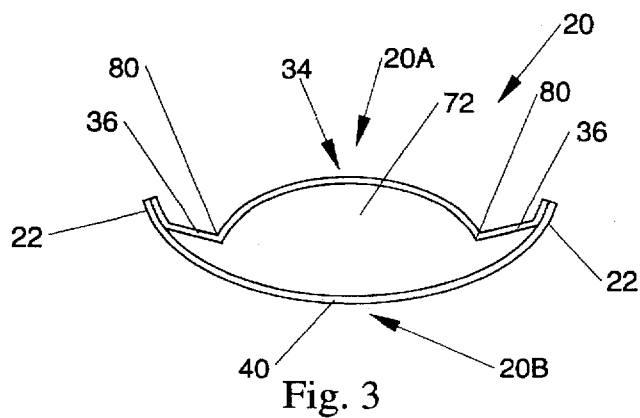
FIG. 3 is a schematic cross-sectional view of the sanitary napkin shown in FIG. 1 taken along line 3—3 (also shown without flaps).
Figure 7:
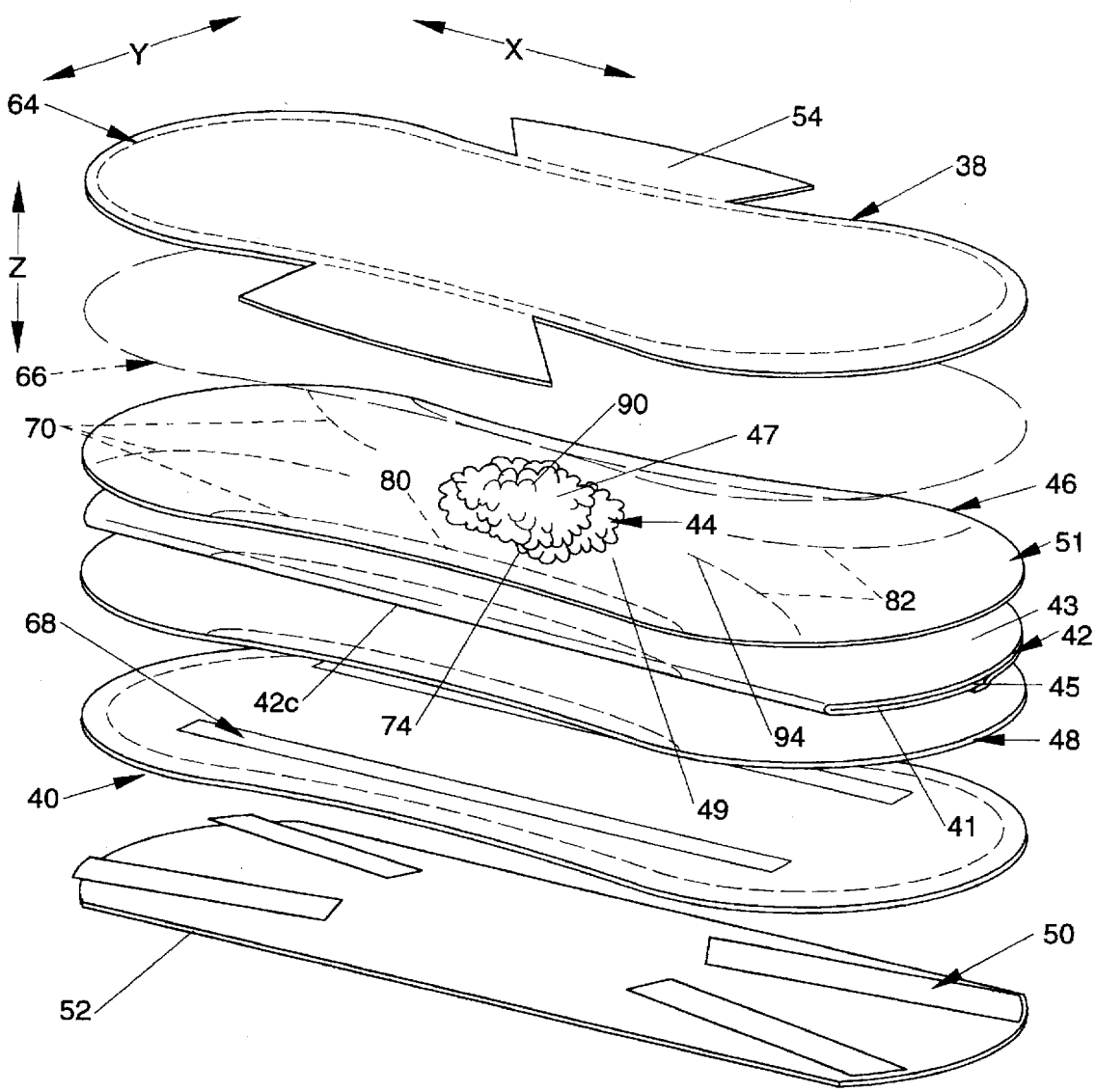
FIG. 7 is an exploded perspective view showing the assembly of one version of the sanitary napkin shown in FIG. 1.

FIG. 7 is an exploded perspective view showing the assembly of one preferred version of the sanitary napkin 20 shown in FIGS. 1—3. As shown in FIG. 7, the sanitary napkin 20 preferably comprises a liquid pervious topsheet 38, a liquid impervious backsheet 40 joined to the topsheet 38, and an absorbent core 42 positioned between the topsheet 38 and the backsheet 40.

The sanitary napkin 20 preferably also comprises certain optional components. These include an optional tufted bundle (or "bun") 44 of capillary channel fibers that is positioned generally on top of the absorbent core 42. The sanitary napkin 20 can also be provided with one or more additional layers or components. These include an acquisition layer (or the "secondary topsheet") 46 positioned generally between the bun 44 of capillary channel fibers and the absorbent core 42. The sanitary napkin 20 also includes a nonwoven layer 48 positioned between the absorbent core 42 and the backsheet 40. The nonwoven layer 48 serves to keep the material of the core 42 from tearing when (the core is comprised of cross-linked cellulose fibers and) the layers of the sanitary napkin are stitched.

The sanitary napkin 20 also includes at least one panty fastener, such as panty fastening adhesive strips 50. An optional release paper 52 may cover the adhesive strips 50. This keeps the adhesives 50 from sticking to surfaces other than the crotch portion of the undergarment prior to use of the sanitary napkin 20.

The sanitary napkin 20 may also include extensions of the topsheet 38 that form longitudinal side edge wraps 54. The embodiment shown in FIG. 7 differs from that shown in FIG. 1 with respect to this feature. FIG. 1 shows a sanitary napkin 20 which includes optional side flaps or "wings" 56. The side flaps or "wings" 56 may be folded around the crotch portion of the wearer's panties. The side flaps 56 (as described in greater detail below) can serve a number of purposes, including, but not limited to protecting the wearer's panties from soiling and keeping the sanitary napkin secured to the wearer's panties. The longitudinal side edge wraps 54, on the other hand, wrap around the other components of the sanitary napkin 20 to provide the sanitary napkin with more comfortable longitudinal side edges 22.

The components of the sanitary napkin 20 may be held together in any suitable manner. In the embodiment shown in FIG. 7, the components of the sanitary napkin 20 will be held together by a perimeter seal 64, a topsheet attachment mechanism, such as topsheet bonding adhesive 66, and a backsheet attachment mechanism, such as backsheet bonding adhesive 68. In addition, in this preferred embodiment, the assembly of the bun 44 of capillary channel fibers, the secondary topsheet 46, the absorbent core 42, and the nonwoven layer 48 is held together by stitching lines 70 to form a core/nonwoven sheet sandwich. The stitching lines 70 preferably form bending axes 80 and 82 for portions of the sanitary napkin to bend about when the sanitary napkin 20 is worn. All of these components and features will be described in greater detail below.

2. Shape of the Sanitary Napkin and Configurations the Sanitary Napkin May Take During Wear A. Shape of the Sanitary Napkin FIGS. 1–3 show that the sanitary napkin 20 has a curved, body-conforming three-dimensional shape.

FIG. 2 shows that the sanitary napkin 20 has a curved longitudinal profile in which the ends 24 of the sanitary napkin are displaced upward. The sanitary napkin 20 has a hump 72 formed by the tuft of capillary channel fibers on its body surface 20A. The sanitary napkin 20 also has a curved transverse profile.

The term "curved", as used herein with reference to the shape of the absorbent articles (as well as the securement mechanisms that retain them in their curved configurations, and the forms used in making the absorbent articles, etc.), is used in its broadest sense in that it includes articles having overall shapes that represent deviations from straight lines or planar surfaces. The articles may comprise curved overall shapes that are formed by one or more curvilinear lines or surfaces, rectilinear lines or surfaces, or combinations of curvilinear and rectilinear lines or surfaces. The term "curved" is, thus, not limited solely to articles formed entirely of a curvilinear segment or segments.

The sanitary napkin is also profiled so that it is thicker in the center of the sanitary napkin and tapers so it becomes thinner toward the edges 22 and 24. The sanitary napkin can be profiled in any suitable amount. Preferably, the sanitary napkin is profiled so that the ratio of the caliper of the sanitary napkin at the intersection of the longitudinal and transverse centerlines to the caliper of the sanitary napkin as measured through the absorbent material at the ends of the sanitary napkin ranges from between about 1.4:1 (e.g., a 7 mm. center and 5 mm. ends) to about 10:1 (e.g., a 20 mm. center and 2 mm. ends).

The sanitary napkin 20 can be profiled by any method known in the art including, but not limited to stacking layers having relatively large length and width dimensions on top of those with smaller length and widths (or vice versa), forming the components of the sanitary napkin in a profiled mold, or by calendaring the components of the sanitary napkin.

The sanitary napkin 20 of the present invention can be curved in any desired amount. The preferred amounts of curvature are discussed with reference to FIGS. 2 and 3.

FIG. 2 shows that the sanitary napkin 20 is preferably curved so that when the central region 32 of the sanitary napkin 20 is placed with the garment surface 20B on a flat surface, the ends 24 of the sanitary napkin 20 are spaced a distance $D_1$ above the plane of the flat surface. Preferably, the curvature of the sanitary napkin 20 is such that the ends 24 are spaced between about 0.5 inch (about 1.3 cm.) or about 1 inch (about 2.5 cm.) to about 1¾ inches (about 4.5 cm.) above the plane of the flat surface.

FIG. 3 shows the lateral (or "cross-machine direction", or "cross-direction") curvature of the sanitary napkin. Preferably, the cross direction curvature of the sanitary napkin 20 is such that when the sanitary napkin is placed on a flat surface, the ends 22 are spaced a distance $D_{1A}$ of between about 5 mm. and about 17 mm. above the plane of the flat surface.

The sanitary napkin 20 can, however, have the amount of curvature provided in any of the sanitary napkins that use elastics for this purpose. Such elasticated sanitary napkins are described in the documents incorporated by reference herein in the "Background of the Invention" section.

In other alternative embodiments, the sanitary napkin 20 can be in other curved configurations. For example, it is possible that the sanitary napkin 20 could be curved in the opposite manner shown in the drawings. In such an embodiment, the center of the sanitary napkin would be displaced upward, and the ends displaced downward when the garment surface 20B of the sanitary napkin is placed down on a flat surface. Such embodiments are possible, but generally less preferred.

B. Configurations the Sanitary Napkin May Take During Wear

The sanitary napkin 20, ideally, is capable of continuous dynamic adjustment during wear. This allows the sanitary napkin 20 to provide sustained close fit against the wearer's body.

There are many features of the sanitary napkin 20 that can provide it with this ability.

The tuft 44 of capillary channel fibers forms a hump 72 which is capable of fitting in the space between the wearer's labia. The hump 72 is preferably tapered so that its sides and ends gradually decrease in elevation as the base of the hump 72 is approached so that it will be comfortable for the wearer. The hump 72 allows the sanitary napkin 20 to intercept body exudates readily when they leave the wearer's body.

The hump 72 preferably has approximately the following dimensions: a length (or x-direction dimension) of about 4–10 cm., more preferably about 2–3 inches (about 5–7.5 cm.)(the length of the hump is also preferably less than or equal to about ½ the length of the absorbent core); a width (or y-direction dimension) at widest point of less than or equal to about 5 cm., more preferably less than or equal to about 1.5 inches (about 3.8 cm.); and, a caliper (or z-direction dimension) of about 5 mm–10 mm. The caliper of the hump at its point of maximum elevation is preferably greater than or equal to about 1.5 times the caliper of the surrounding longitudinal edge regions and end regions of the sanitary napkin. The hump 72 is preferably tapered so that its point of maximum caliper extends less than or equal to about ¾ the width of the hump 72.

The hump 72 is useful in placing the capillary channel fibers in the bun 44 in close proximity to the wearer's body. This is particularly true for the capillary channel fibers located in the upper portion of the bun 44. These fibers, as described in greater detail below, are preferably oriented in the z-direction. This allows these capillary channel fibers to draw liquids away from the wearer's body and down into the absorbent core. The capillary channel fibers that comprise the hump 72 are also particularly useful in pumping liquids into the portions of the core 42 that are elevated due to the curvature of the sanitary napkin 20.

The fit in the space between the wearer's labia is enhanced when the hump 72 is formed from materials, such as capillary channel fibers, which are resilient. Preferably, the materials forming the hump 72 are both resilient when wet and dry. The resiliency allows the hump 72 to adapt to the space between the wearer's labia more readily when the wearer moves about.

Figure 4:
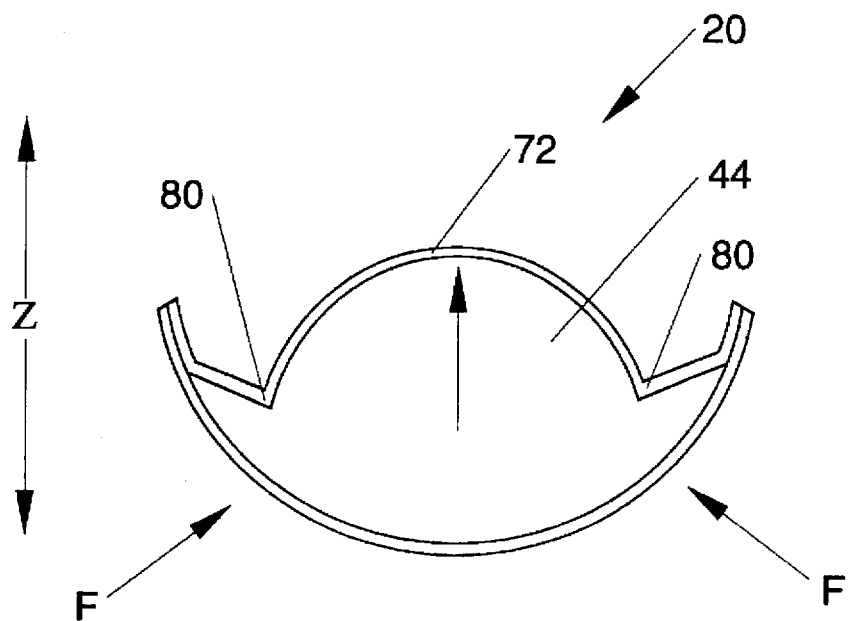
FIGS. 4 and 5 are cross-sectional views similar to that of FIG. 3 showing the effect of laterally oriented compressive forces on the sanitary napkin.
Figure 5:
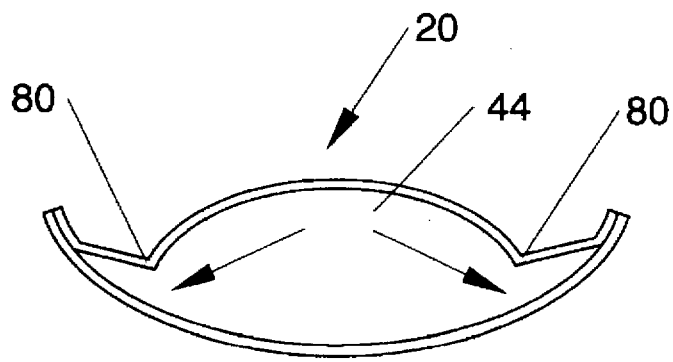

FIGS. 4 and 5 show that the sanitary napkin 20 is preferably capable of adjusting in response to the laterally inwardly oriented compressive forces exerted on it during wear.

FIG. 4 shows the configuration the sanitary napkin 20 may take under laterally inward-oriented compressive forces F applied to the sanitary napkin 20. Such forces are typically applied by the insides of the upper portions of the wearer's thighs when the sanitary napkin 20 is worn. The compressive forces F cause the sanitary napkin 20 to bend about bending axes 80 (this bending is described in greater detail below) and the bun 44 rise. Preferably, this will result in improved contact of the bun 44 with the wearer's body.

FIG. 5 shows a configuration the sanitary napkin 20 may take when the laterally inwardly-oriented compressive forces are removed. The resiliency of the capillary channel fiber bun 44 and the controlled bending of the absorbent core in the central portion 32 of the sanitary napkin tend to return the sanitary napkin 20 to its original shape when the lateral compressive forces are removed. The adaptation of the sanitary napkin to these forces avoids undesirable distortion (such as roping) of the sanitary napkin during use. This helps maintain the sanitary napkin in contact with the wearer's body, and coverage of the desired area of the wearer's panties.

Figure 6:
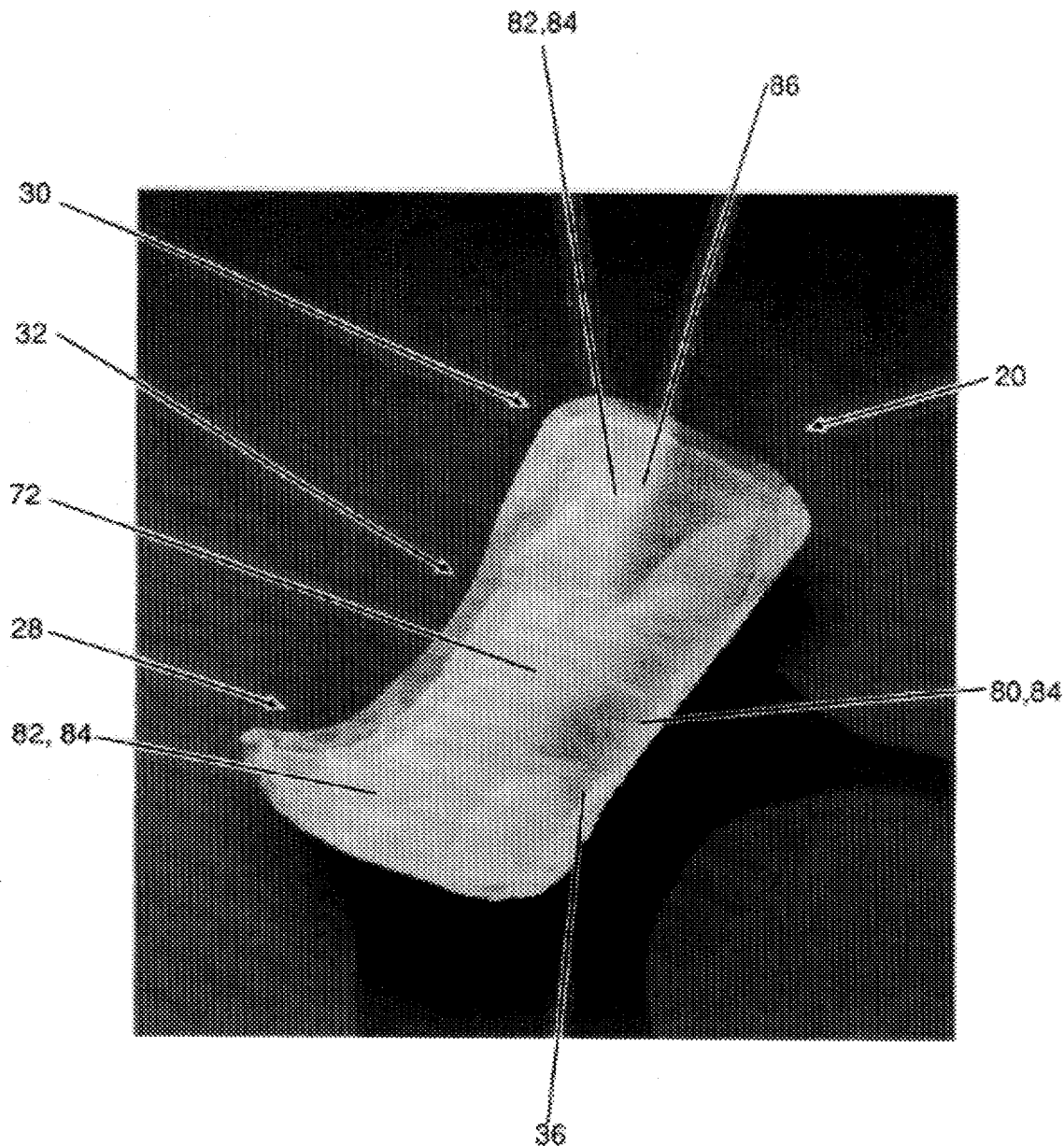
FIG. 6 is a perspective view of the sanitary napkin of the present invention in one possible in-use configuration.

FIG. 6 shows that the central region 32 of the sanitary napkin 20 containing the hump 72 is also preferably provided with the ability to separate (or "decouple") from the wearer's panties or the other components of the sanitary napkin. This provides the hump 72 with the ability to move into close contact with the wearer's labia when the wearer's panties move in a direction away from the labia during wear.

In the embodiment shown in FIG. 6, this is achieved by providing the sanitary napkin 20 with a particular panty fastener configuration. The sanitary napkin is provided with panty fasteners in the end regions 28 and 30. The sanitary napkin 20, however, is not provided with panty fasteners in the central region 32. This allows the central region 32 containing the hump 72 to decouple from the wearer's panties and move toward the wearer's labia.

In other embodiments, the sanitary napkin 20 can have other types of decoupling mechanisms. For instance, the sanitary napkin can have elements that decouple by some movement within the sanitary napkin instead of having the backsheet 40 decouple from the wearer's panties. These other decoupling features can be used instead of, or in addition to the adhesive pattern which provides decoupling of the backsheet 40 from the wearer's panties.

Particular types of decoupling of the elements of an absorbent article are described in U.S. Pat. No. 5,007,906 which issued to Thomas W. Osborn, et al. on Apr. 16, 1991; EPO Patent Application Publication No. WO 92/07535 entitled "Sanitary Napkin Having Components Capable of Separation in Use" published May 14, 1992 in the name of Visscher, et al.; and, in U.S. patent application Ser. No. 07/874,872 entitled "Generally Thin, Flexible Sanitary Napkin With Stiffened Center" filed Apr. 28, 1992 in the name of Osborn. The European patent application above discloses (among other things) a sanitary napkin having a spacing structure capable of decoupling from the absorbent core of the sanitary napkin. The pending U.S. patent application discloses a sanitary napkin having a central absorbent hump which is capable of decoupling from the absorbent core of the sanitary napkin, among other things.

The bending axes 80 and 82 are another feature that provides the sanitary napkin 20 with the ability to provide sustained close fit against the wearer's body. The bending axes 80 and 82 allow the sanitary napkin 20 to be formed into specific configurations when worn. The bending axes 80 and 82 in the embodiment shown in FIGS. 1 and 7 are formed by stitching lines 70 and/or densified or embossed areas 84 that preferably correspond in location with the stitching lines 70. The bending axes 80 and 82 in the embodiment shown in FIGS. 1 and 7 are of two general types.

The first type of bending axes comprises a pair of bending axes 80 located generally at least in the central region 32 of the sanitary napkin 20. The first type (or pair) of bending axes 80 preferably comprises a pair of longitudinally oriented curved convex inwardly-oriented axes. The first pair of bending axes 80 are located in the longitudinal side regions 36 of the sanitary napkin 20. The longitudinal side regions 36 are generally thinner and more flexible than the portion of the central region 32 containing the hump 72. The first pair of bending axes 80 are located between the base 74 of the hump 72 and the longitudinal side edges 42C of the absorbent core 42.

The first pair of bending axes 80 serve to encourage the sanitary napkin 20 to bend about the base 74 of the hump 72 when the sanitary napkin 20 is subjected to laterally inwardly oriented compressive forces such as those exerted on the sanitary napkin 20 by the upper portions of the wearer's thighs. The configuration of the first pair of bending axes 80 will preferably fit the insides of the upper portion of the wearer's thighs.

The second type (or set) of bending axes 82 are located primarily in the end regions 28 and 30 of the sanitary napkin 20. The second set of bending axes 82 preferably comprises four curved convex inwardly-oriented bending axes. The four axes 82 are preferably arranged so that they each originate from the base 74 of the hump 72 and run in a direction from the intersection of the longitudinal and transverse centerlines, C, to one of the corners 27 of the sanitary napkin 20.

The overall configuration of the second set of bending axes 82 preferably corresponds generally to the configuration of the panty fastener (though this is not absolutely required). This provides for maximum conformation about these axes during wear. The individual bending axes, however, may, but preferably do not extend as far toward the corners 27 of the sanitary napkin 20 as the panty fasteners. This is because (as described in greater detail below) the second set of bending axes 82 may also serve a liquid transporting function.

The first and second sets of bending axes 80 and 82 described herein are in one preferred configuration. In alternative embodiments, the sanitary napkin 20 may be provided with bending axes in many other configurations.

The sanitary napkin 20 may, for instance, be provided with a third bending axis such as that designated by reference number 86 in FIG. 6. The third bending axis 86 preferably lies along at least a portion of the longitudinal centerline L of the sanitary napkin 20. The third bending axis 86, like the other bending axes, can be formed in any suitable manner, such as by folding the sanitary napkin.

The third bending axis 86 may be used to provide the desired fit of the end regions 28 and 30 of the sanitary napkin adjacent the wearer's body. The third bending axis 86 may also be used in the central region 32 of the sanitary napkin 20 to cause the central region to be predisposed to bend upward.

The caliper and flexibility of the various portions of the sanitary napkin 20 also provide the sanitary napkin with the ability to fit closely against the wearer's body. The end regions 28 and 30 of the sanitary napkin 20 are preferably thinner and more flexible that the portion of the central region 32 containing the hump 72. The end regions 28 and 30 (and the aforementioned longitudinal side regions 36) preferably have calipers and flexure-resistances within the range of those specified for the sanitary napkins described in the above-mentioned pending U.S. patent application Ser. No. 07/874,872, and in U.S. Pat. Nos. 4,950,264 and 5,009,653 issued to Osborn on Aug. 21, 1990 and Apr. 23, 1991, respectively. (In other embodiments, it is possible that the caliper and flexibility of the end regions 28 and 30 may be more or less.)

The higher flexibility of the end regions 28 and 30 can be attributed to several factors. It can result from the reduced caliper of these regions. In addition, in a preferred embodiment, the flexibility of the end regions 28 and 30 may be increased by performing a mechanical operation, such as ring rolling, on the end regions 28 and 30.

The terms "ring rolling" (or "pre-corrugating"), as used herein, refer to a mechanical operation that involves passing a material between meshing corrugated rolls, or the like. Ring rolling the end regions creates folds in the end regions that provide the end regions with a plurality of bending axes for greater flexibility. The folds are also able to stretch open when the sanitary napkin 20 is worn.

Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent Application Ser. No. 07/662,536 filed by Gerald M. Weber et al. on Feb. 28, 1991, U.S. patent application Ser. No. 07/662,537 filed by Kenneth B. Buell et al. on Feb. 28, 1991, and U.S. patent application Ser. No. 07/662,543 filed by Gerald M. Weber et al. on Feb. 28, 1991 (collectively referred to herein as the "Ring Rolling" patent applications).

The end regions 28 and 30 are preferably ring rolled so that the fold lines in the corrugations formed therein run generally in the longitudinal direction. In other embodiments, the fold lines could run in the transverse direction, both directions, and/or other directions.

The benefit of providing the end regions 28 and 30 of the sanitary napkin 20 with increased flexibility and the second set of bending axes 82 (and the other features described above) is discussed with relation to FIG. 6.

The sanitary napkin 20 is able to conform to the three basic regions of the wearer's body that the sanitary napkin 20 contacts when the sanitary napkin 20 is worn.

The body of the wearer may be divided into three anatomically distinctly-shaped regions when the wearer is viewed along the longitudinal axis. From the front of the wearer's body to the back of the wearer's body, the first of the three regions is the mons region. The mons region has a compound curved convex upward shape. The second region is that containing the vaginal introitus. The second region is defined by the labia majora and resembles a W-shaped outline. The third region is determined by the crevice between the buttocks (or "gluteal groove") and is generally cusp-shaped and defined by two convex upward and outwardly diverging lines. (The characteristics of these parts of the body are described in greater detail in U.S. patent application Ser. No. 07/630,451 entitled "Sanitary Napkin Having Transversely Segmented Core" filed in the name of Osborn on Dec. 19, 1990.)

The sanitary napkin 20 preferably adapts to these three very distinct shapes of the wearer's body in the following manner.

The high flexibility of the first end region (or "front end region") 28 of the sanitary napkin 20 allows this portion of the sanitary napkin to curve around the convex upward shape of the mons region. The pair of bending axes in the second set of bending axes 82 located in the first end region 28 aids the first end region 28 in bending around the mons region.

The central region 32 of the sanitary napkin 20 is able to conform closely to the shape of the wearer's labia majora. This can occur even though the central region 32 may be less flexible than the end regions 28 and 30. This is because the hump 72 can fit comfortably within the space between the labia majora. The bending of longitudinal side regions 36 upward about the first pair of fold axes 80 allows the central region 32 to assume a W-shape outline to closely fit the second region of the wearer's body.

The second end region (or "rear end region") 30 of the sanitary napkin 20 is also flexible. This flexibility and the pair of bending axes in the second set of bending axes 82 located in the second end region 30 aids the second end region 30 in bending upward in a cusp shape to provide close contact with the wearer's gluteal groove.

The various regions of the sanitary napkin 20, as noted above, can also be provided with densified areas, such as densification lines 84.

These densified areas 84 can be provided by the stitching lines 70 used to secure various components of the sanitary napkin together. Alternatively, or additionally, the sanitary napkin 20 can be embossed, or the like, to provide the densified areas.

The densification of the sanitary napkin 20 in chosen areas can serve a number of purposes. These include, but are not limited to the following. The densified areas can, as noted above, be used to form bending axes to aid the sanitary napkin in assuming particular in use configurations. The densified areas can be used to create higher capillarity in selected parts of the sanitary napkin 20 for transporting liquids in the z-direction. The densified areas can also be used to create channels capable of transporting liquids in the x-y plane to selected portions of the sanitary napkin 20.

The densified areas 84 are also useful in sanitary napkins to control stain patterns. It has been found that some women prefer that the menses stain be confined to certain portions of a sanitary napkin. These women feel more confident in a product that gives the visual appearance of controlling the flow of menses within the sanitary napkin. Thus, the densification areas can provide a positive consumer signal.

The densified areas 84 in the embodiment shown in FIG. 1 are in the same pattern as the stitching lines 70. The densified areas 84 can be provided in any suitable pattern, however. Such patterns need not coincide with stitching lines, and the like. For example, the densification lines 84 may be in the form of an oval or hexagon around the base of the hump 72.

The individual components of the sanitary napkin will now be looked at in greater detail.

3. The Individual Components of the Sanitary Napkin

A. The Topsheet

The topsheet 24 is compliant, soft feeling, and non-irritating to the wearer's skin. Further, the topsheet 24 is liquid pervious permitting liquids (e.g., menses and/or urine) to readily penetrate through its thickness.

The topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has two longitudinal edges 38C and two end edges 38D.

(A similar numbering system will be used for the other components of the sanitary napkin. That is, the side of the component facing the wearer's body will be designated by the number of the component and a reference letter "A". The side facing the wearer's undergarments will be designated by the number of the component and the letter "B" The side and end edges will be designated by the number of the component and the reference letters "C" and "D" respectively.)

A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135, entitled which issued to Thompson on Dec. 30, 1975; U.S. Pat. No. 4,324,246 which issued to Mullane, et al. on Apr. 13, 1982; U.S. Pat. No. 4,342,314 which issued to Radel. et al. on Aug. 3, 1982; U.S. Pat. No. 4,463,045 which issued to Ahr et al. on Jul. 31, 1984; U.S. Pat. No. 4,629,643 issued to Curro, et al. on Dec. 16, 1986; and U.S. Pat. No. 5,006,394 issued to Baird on Apr. 9, 1991. The preferred topsheet for the present invention is the formed film described in one or more of the above patents and marketed on sanitary napkins by The Procter & Gamble Company as "DRI-WEAVE".

In a preferred embodiment, the topsheet 38 is hydrophilic so that liquids will transfer through the topsheet 38 faster than if it was not hydrophilic. This will diminish the likelihood that body exudates will flow off the topsheet rather than being absorbed by the absorbent core. Such topsheets (as well as fibrous topsheets) can be rendered hydrophilic by treating them with surfactants. Suitable methods of applying surfactants are described in U.S. Pat. Nos. 4,950,254 and 5,009,653 issued to Osborn, and in U.S. patent application Ser. No. 07/794,745, P&G Case 4528, filed on Nov. 19, 1991 by Aziz, et al.

The topsheet 38 may be stretched and secured to another component and relaxed to provide the sanitary napkin 20 with curvature (as described in detail below). If a formed film is used as the topsheet in such a process, the shape or pattern of apertures in the film could be varied to impart more/less elasticity to the topsheet. The degree of lengthwise and cross-direction curvature can also be varied with the elasticity and other physical properties of the topsheet. (The same applies to any of the other components of the sanitary napkin that may be stretched to create a curved product.)

It will also be appreciated that fibrous, nonwoven topsheets made from materials such as polyethylene, polypropylene and blends are commonly used in commercial sanitary napkins and pantiliners, and such fibrous topsheets can also be used herein. A nonwoven with elastic properties could, therefore, be used as the topsheet in products where the topsheet 38 is stretched to create a curved product.

Such fibrous topsheet materials which can be used herein include, for example, various nonabsorbent fibrous or filamentous network sheets which are aqueous-fluid-permeable by virtue of a multiplicity of holes or channels passing therethrough. Such sheet materials are described in U.S. Pat. No. 4,636,419, Madsen et al, Jan. 13, 1987 and European Patent Application 0215417, filed Jun. 9, 1986, Sneyd et al.

B. The Absorbent Core (1) General

The absorbent core 42 is an absorbent means which is capable of absorbing or retaining liquids such as vaginal fluids (e.g., menses) and other certain body exudates. The absorbent core 42 is shown best in FIG. 7. The absorbent core 42 has a body surface, a garment surface, side edges, and end edges.

The absorbent core 42 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt.

Examples of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 42 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 42 should, however, be compatible with the design loading and the intended use of the sanitary napkin 20. Further, the size and absorbent capacity of the absorbent core 42 may be varied to accommodate different uses such as incontinence pads, pantiliners, regular sanitary napkins, or overnight sanitary napkins.

Exemplary absorbent structures for use as the absorbent core of the present invention are described in U.S. Pat. Nos. 4,950,264 and 5,009,653 entitled "Thin, Flexible Sanitary Napkin" issued to Osborn on Aug. 21, 1990 and Apr. 23, 1991; U.S. Pat. No. 4,610,678 entitled "High-Density Absorbent Structures" issued to Weisman et al. on Sept. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al.

(2) The Cross-Linked Cellulose Fiber Laminate Core

A preferred embodiment of the absorbent core comprises the laminate structure shown in FIG. 7. The laminate is comprised of a layer of superabsorbent polymeric material (or absorbent gelling material) and one or more sheets or webs of cross-linked cellulosic fibers.

Suitable cross-linked cellulose fibers for the absorbent core are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,898,642, issued Feb. 6, 1990 to Moore, et al.; and U.S. Pat. No. 4,935,022 issued Jun. 19, 1990 to Lash et al.; EPO Patent Application Publication Nos. 0 427 316 A2 and 0 427 317 A2 published in the name of Herron, et al. on May 15, 1991; and EPO Patent Application Publication No. 0 429 112 A2 published in the name of Herron, et al. on May 29, 1991.

The cross-linked cellulosic fibers in the embodiment shown in FIG. 7 comprises a single sheet that wraps the layer of particles 41 of absorbent gelling material. The sheet is wrapped so that it appears as having an "e" (or reverse "e" configuration) when viewed from the end. The wrapped sheet forms an upper layer 43 and a lower layer 45. In alternative embodiments, the laminate can be formed in many other manners, such as by providing separate webs of cross-linked cellulosic material (or other absorbent material) for the different layers of the absorbent core laminate rather than a single sheet, or by providing it with additional layers.

In this type of core, curled, twisted, preferably chemically stiffened and crosslinked, cellulose fibers are refined to provide fibers which can be used in sheet form as the absorbent core. The preparation of suitable curled, chemically stiffened cellulosic fibers from which one can prepare the refined, curled, chemically stiffened cellulosic fibers used in the practice of this invention is described in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations preferably involve the use of aldehydes, such as glutaraldehyde, as crosslinking agents. In addition, polycarboxylic acids can be used as crosslinking agents. Reference can be made to the various citations in U.S. Pat. No. 4,898,642 and PCT U.S. 89 01581 for other cross-linked fiber types. Once in hand, the curled cellulosic fibers are refined to provide the fibers used to prepare the preferred absorbent cores used in the practice of this invention.

In a typical refining process, an aqueous stock comprising about 3% by weight of the curled cellulosic fibers and 97% by weight water is passed through a Sprout-Waldron (now available as Sprout-Bauer) single disk refiner (available from Koppers Company, Inc., Muncy, Pa. Model 105A-LAB) using deknotting disk of the 17804-A type. An objective of the refining process is it cut the twisted fibers without substantially defibrillating them.

The 3% aqueous stock solution is diluted to 0.5% consistency. The solution flows through the Sprout-Waldron refiner using a gap setting of from about 5 mils to about 30 mils. Preferably, the gap setting is about 2.5 mils. The Sprout-Waldron refiner is modified by removing the equalizing spring so that the gap setting remains constant throughout the flow of the fibrous stock solution. A typical flow rate through the refiner is 9-10 gallons per minute. The refining amperage is about 45 on a 25 hp. motor. (The use of the amperage term is a measure of the mechanical energy imparted to the fibers during the refining.) A single pass of the fibers through the gap is employed.

In an alternate mode, the curled cellulosic fibers can be used in combination with crill. Crill is refined southern softwood kraft fiber having a Canadian standard freeness between about 50 to about 100 ml. (TAPPI standard). Typically, the crill comprises up to about 5%–10% by weight of the curled cellulosic fibers. Addition of crill can impart desirable strengthening properties to the final sheets, and also can serve as a diluent in the sheets, for reasons of economy.

Following the refining, the 0.5% aqueous slurry of the refined, twisted fibers is further diluted to a slurry weight of from about 0.1%–0.2% for use in the formation of sheets.

The in-use integrity of absorbent structures comprising the refined, curled fibers disclosed above can be further enhanced by ultrasonic or heat bonding, especially in conjunction with the use of 10–15% by weight of thermoplastic fiber (e.g., KODEL 410 polyester) admixed with the refined fibers. In yet another method, various spot-bonding means can be employed to affix the backsheet to the core, especially over those areas to which the panty-fastening adhesive is applied.

C. The Backsheet

The backsheet 40 prevents the exudates absorbed and contained in the absorbent core 42 from wetting articles which contact the sanitary napkin 20 such as pants, pajamas and undergarments. The backsheet 40 is impervious to liquids (e.g., menses and/or urine). The backsheet 40 is preferably manufactured from a thin plastic film, although other flexible liquid impervious materials may also be used. As used herein, the term "flexible" refers to materials which are compliant and will readily conform to the general shape and contours of the human body.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., with pantiliner devices herein.

D. The Capillary Channel Fiber Bun

The sanitary napkin 20 preferably has a tufted bundle (or "bun") 44 of capillary channel fibers 90 that are positioned generally on top of the absorbent core 42.

That is, the tufted portion of the bundle of fibers is typically positioned on top of the core 42. The lower portions of the bundle of fibers may, but need not, also be positioned on top of the core 42. The lower portions of the bundle of fibers are preferably inserted within the core 42 or positioned under the absorbent core 42.

The tuft can be formed by forming the fibers in the upper portion of the bundle of fibers into a loop. These fibers are then retained in their looped configuration by some suitable mechanism. The loop of fibers can also be manipulated in various ways to provide it with desired characteristics. For instance, the loop can be turned or twisted (such as by a half turn applied to the loop) to provide a structure that is more resilient and less subject to collapse during use. (The twisting typically refers to applying x-y plane rotational forces on the loop.)

Figure 7A:
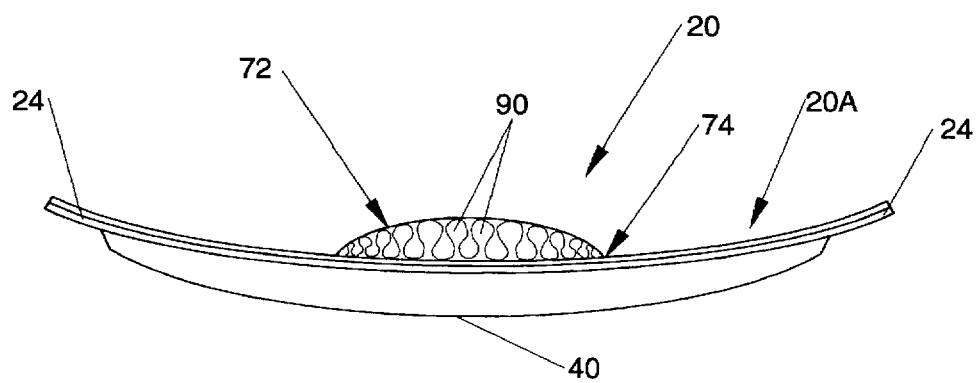
FIG. 7A is a schematic side view similar to FIG. 2, only with the topsheet and secondary topsheet removed to show an embodiment of the capillary channel fiber bun that comprises a plurality of tufts of fibers.

In another embodiment (shown in FIG. 7A), the central portion of the layer of capillary channel fibers can be gathered into a plurality of small "loops" or "tufts" These loops or tufts extend upward from the layer of capillary channel fibers to firmly contact the topsheet. Moreover, the loops or tufts are positioned centrally in the overall article, such that it can provide rapid acquisition and transport of fluid into the remaining portion of the layer of capillary channel fibers, and thence into the fluid storage layer of the article.

Advantageously, such "loop" or "tuft" not only concentrates capillary channel fibers at the point where fluid impinges onto the article, but also orients the capillary channel fibers which comprise the loop or tuft substantially in the upward z-direction, thus enhancing fluid movement in the downward z-direction of the article.

Capillary channel fibers are fibers having channels formed therein, preferably, on their exterior surfaces. FIGS. 8 to 11C show examples of some types of capillary channel fibers 90.

Suitable capillary channel fibers are described below, and in the following patent applications which were filed on Jul. 23, 1991: U.S. patent application Ser. No. 07/734,404 filed in the names of Thompson, et al.; U.S. patent application Ser. No. 7/734,392 filed in the names of Thompson, et al.; and, U.S. patent application Ser. No. 07/734,405 filed in the names of Buenger, et al. These patent applications may be referred to collectively as the "Capillary Channel Fiber" patent applications. Suitable capillary channel fibers are also described in EPO Patent Application 0 391 814 published Oct. 10, 1990.

While a variety of capillary channel fibers can be used herein, the following description discusses some preferred characteristics of the capillary channel fibers 90 that are incorporated into the absorbent articles of this invention.

(1) Fiber Morphology

The capillary channel fibers 90, as noted above, have capillary channels 92 on their outer surfaces. While the capillary channel fibers can also have a hollow central core which would provide some additional capillarity, it is preferred that such hollow core fibers not be employed.

In general, providing capillary channel fibers with a central hollow core would require the fibers to be somewhat stiffer than desired so that the central core will not collapse under pressure. A central core running through a capillary channel fiber would also not be expected to quickly pick up and deliver liquids, since the liquids would have to find their way to the end of a fiber before proceeding into the central core, and to deliver liquids the end of the capillary channel fiber would always have to be in direct contact with the absorbent core material.

The capillary channel fibers 90 are preferably either bent or, more preferably, in a curled configuration (that is, they are nonlinear). Most preferably, the capillary channel fibers 90 are "substantially curled" (or otherwise gathered). This provides the capillary channel fibers with a higher loft and increased resilience for a given number of fibers. The capillary channel fibers 90, however, should preferably not be "kinked". Kinking a capillary channel fiber can cause points of constriction of the capillary channels at each kinking site. This will interfere with fluid flow dynamics along the capillary channel.

Figure 12:
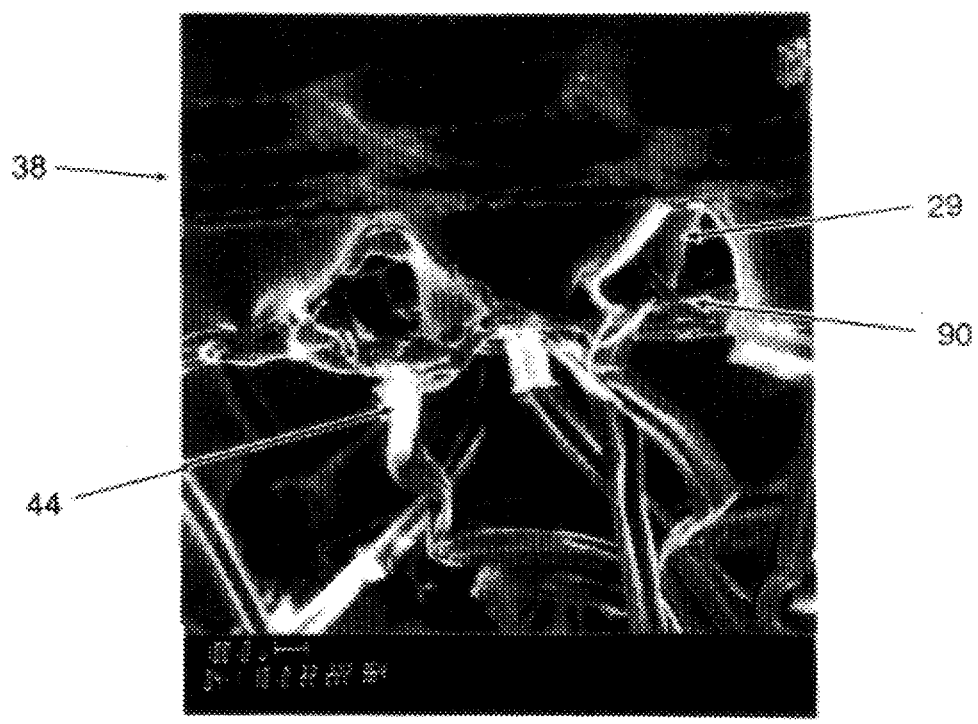
FIG. 12 is a photomicrograph sectional view of part of a sanitary napkin which shows the close contact between a formed film topsheet and an underlying layer of capillary channel fibers and the protrusion of capillary channel fibers into the pores of the topsheet.

In addition, there is another substantial advantage to employing nonlinear capillary channel fibers. FIG. 12 shows that it may be preferred that small portions, or "tufts", of the capillary channel fibers 90 actually protrude into at least some of the topsheet 38 orifices 29 of the articles herein. These protrusions are easier to effect when a high loft capillary channel pad is prepared using curled capillary channel fibers. There is a greater likelihood that a number of ends and/or curls in the capillary channel fibers will find their way into the orifices of the topsheet material than if substantially linear capillary channel fibers were to be employed.

The capillary channel fibers 90 may be curled in a number of ways, including, but not limited to: (1) selectively heat quenching the fibers as they come from their forming die; (2) fibers made from synthetic polymers such as polyesters can be curled by stretching, followed by relaxation, or by passing the fiber under tension around a sharp edge, followed by relaxation; or (3) by immersion in methanol. In a preferred mode, the fibers are substantially helical. Whatever means are used to crimp or otherwise gather the capillary channel fibers, they can, if desired, be carded to form an assembly of fibers.

The preferred amplitude of the curls is in the range of about 0.1 mm to about 3 mm, and, typically, the frequency of the curls is from about 0.5 per cm of fiber to about 5 per cm of fiber. Fibers with amplitudes of about 3 mm and a frequency of about 0.5 per cm exhibit good softness even in the higher denier ranged fibers having large capillary channels. Stated otherwise, an average capillary channel fiber having a straight-line length of about 2 cm is curled or gathered to provide optimal fibers having a length of from about 0.5 cm to about 1.5 cm.

The capillary channel fibers 90 are intended to promote passage of liquids in the "z" direction of absorbent articles. This is shown with reference to FIG. 7. FIG. 7 shows that the long (or "x") axis is referred to as the "machine direction", inasmuch as, during manufacture the articles pass through the machine in the direction of this axis. The short (or "y") axis is referred to as the "cross direction", since it is the direction across the width of the article. The "z" direction is the direction proceeding down through the topsheet, thence into the layer of capillary channel fibers, and thence into whatever fluid storage core that may be provided.

The objective is to provide a gradient of capillary suction between the topsheet 38 and underlying layer or layers of the articles herein, such that liquid is drawn in the "z" direction and away from the surface of the article into its ultimate storage layer. Empirically, capillary suction is related to adhesion tension and inversely related to the size of the openings—i.e., in the typical case, the openings in the topsheet will be larger than the intra-fiber capillary channels, which, in turn, will be larger than the inter-fiber capillary channels in a fibrous storage core. The surface hydrophilicity of the components of each layer can also theoretically affect the capillary suction gradient.

The capillary channel fibers 90 in at least the upper portion 47 of the tuft 44 are preferably oriented generally in the z-direction. The ends of the looped capillary channel fibers in the tuft may be cut to provide a fleece-like, z-directional bundle of open-ended capillary channel fibers.

Further, by providing some underlying capillary channel fibers that lie substantially parallel to the machine direction, fluid flow in the machine direction is also promoted, which enhances the overall useful absorbency of the article. Further, by orienting the capillary channel fibers of the lower portion 49 of the tuft 44 in the machine direction, fluid flow in the cross direction is controlled, thereby minimizing, or even entirely avoiding, leakage of fluid from the longitudinal side edges 22 of the article.

Thus, unlike absorbent articles of the prior art which utilize fibrous batts which comprise inter-fiber capillary voids and move liquids in an undirected manner in the x, y and z directions, the intra-fiber capillary channels 92 of the capillary channel fibers 90 can be used to provide desirable fluid directionality. In addition, since the capillary of the fibrous layer of the present invention resides in the fibers 90 themselves, rather than in inter-fiber spacings, capillarity is not lost when fiber-fiber spacings become displaced.

In addition, the capillary channel fiber bun 44 of the present invention provides its liquid drawing and directing functions even when the bun 44 is soft, fluffy and comfortable to the wearer, in contrast to compact, dense and relatively stiff batt materials which function by inter-fiber capillary action.

While it will be appreciated by those familiar with the physics of fluid transport that the absorbent articles described herein conveniently make use of the differences in spacings between topsheet, capillary channel fibers and core to establish a pressure gradient to draw fluids in the z-direction, other means can be employed to establish such z-direction fluid-flow gradient. For example, if the holes or spacings in the topsheet are smaller than the width of the capillary channel fibers (and such intra-fiber channel widths as wide as 90 microns may be useful for transporting relatively thick fluids such as menses), then the desired gradient can be established, for example, by selecting a topsheet which is more hydrophobic than the capillary channel fibers.

(2) Capillary Channel Fiber Structure and Surface Properties

The capillary channel fibers 90 can be prepared from any convenient polymer which is nonswelling when wet. Polymers such as polyethylene, polypropylene, polyesters (preferred), and the like, are useful herein, so long as they are spinnable such that they can be formed with external capillary channels. Conveniently, the polymers are melt-extrudable. Typically, the capillary channel fibers herein will be prepared from a synthetic polyethylene terephthalate polymer melt having an inherent viscosity ("IV") of from about 0.6 to about 0.9. (IV is a term of art and can be determined in well-known fashion. See, for example, U.S. Pat. No. 4,829,761 at column 8.)

The capillary channel fibers 90 preferably have a denier (denier per filament "dpf") of about 10 (at an IV of about 0.9)–22 (at an IV of about 0.7). However, it is to be understood that the denier of the fibers used is within the discretion of the formulator, and the denier can easily be in the range of 25.

The depth:width ratio of the capillary channels herein is preferably about 2.0, but processing restrictions, as well as for economic reasons, a depth:width ratio of about 1.3 is typically employed. Typical and readily producible capillary channel fibers which are quite satisfactory for use herein thus have a depth-of-walls of about 48 microns and a width-between-walls of about 37 microns. The walls, themselves, are typically about 3–15 microns thick. Although variations in these dimensions are acceptable, capillary channel fibers prepared from polyester and having these characteristics are quite effective for their intended purpose.

Such fibers can be prepared using conventional operating equipment and readily withstand pressures of the type encountered in sanitary devices, especially sanitary napkins and pantiliners, without collapse or spreading of the capillary channel walls to such an extent that their capillary function is lost.

The capillary channels 92 can be of various shapes. Certain shapes can offer particular advantages in particular product applications. For example, "U-shaped", "H-shaped", and "V"-shaped capillary channel fibers 90 may be used. The "H-shaped" fibers are one preferred shape. Furthermore, the basic shapes may be repeated (see Figures), or even branched, to produce fibers containing multiple channels. The multiple "U" fibers of FIG. 10 offer the additional advantages of having additional capillarity due to face-to-face contact and being easily curled.

The modified "C" shaped fibers shown in FIG. 11 are described in greater detail in co-pending U.S. patent application Ser. No. 07/918,174 entitled "Spinerette Orifices and Filament Cross-Sections With Stabilizing Legs Therefrom", filed in the name of Phillips, et al. on Jul. 23, 1992.

The manufacture of capillary channel fibers of the type employed herein is described in EPO Application 391,814 (cited above) and in co-pending U.S. Continuation-In-Part Application entitled "FIBERS CAPABLE OF SPONTANEOUSLY TRANSPORTING FLUIDS", Ser. No. 07/736,261, filed Jul. 23, 1991, Inventors Phillips, Jones, et al, Eastman Chemical Company, and in the co-pending U.S. Patent Application entitled "OPEN CAPILLARY CHANNEL STRUCTURES, IMPROVED PROCESS FOR MAKING CAPILLARY CHANNEL STRUCTURES, AND EXTRUSION DIE FOR USE THEREIN", Ser. No. 07/482,446, filed Feb. 20, 1990, Inventors Thompson and Krautter.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers used herein are surface-treated in order to render them hydrophilic.

The surface treatment of polymeric fibers involves processes which are well-known in the extensive fiber literature. In general, such processes involve treating the surface of the fibers with a "hydrophilizing agent", especially a surfactant. The hydrophilizing agents are preferably added to the polymer to drawing of the capillary channel fibers to their final size. Typical surfactants useful in such processes include various nonionic and anionic detersive surfactants of the general type known in the laundry literature.

Hydrophilizing agents include wetting agents such as polyethylene glycol monolaurates (e.g., PEGOSPERSE 200 ML, a polyethylene glycol 200 monolaurate available from Lonza, Inc., Williamsport, Pa. USA), and ethoxylated oleyl alcohols (e.g., VOLPO-3, available from Croda, Inc., New York, N.Y., USA).

Other types of hydrophilizing agents and techniques can also be used, including those well known to those skilled in the fiber and textile arts for increasing wicking performance, improving soil release properties, etc.

(3) Arrangement of the Capillary Channel Fibers Into Fibrous Batts

In general, the capillary channel fibers 90 will be laid down into a bundle of such fibers for use in the absorbent article. In a preferred embodiment, the bundle 44 of capillary channel fibers is laid down in a batt and gathered into a tuft to form the hump 72.

Such batts will typically have a caliper in the range from about 0.1 in. (0.25 cm) to about 0.7 in. (1.78 cm), preferably from about 0.1 in (0.25 cm) to about 0.4 in. (1 cm) for use in sanitary napkins; preferably from about 0.05 in. (0.13 cm) to about 0.15 in. (0.4 cm) for use in pantiliners; and preferably from about 0.1 in. (0.25 cm) to about 0.5 in. (1.3 cm) for use in infant diapers or adult incontinence garments.

For use in disposable absorbent articles, such batts will typically have from about 0.003 g to about 0.016 g of fiber per 1 $cm^2$ surface area, and will have from about 0.003 g to about 0.03 g capillary channel fiber per 1 $cm^3$ volume (measured in the uncompressed state). The amounts of fiber per unit area and per unit volume for pantiliners, diapers and adult incontinence garments can be calculated based on the differences in caliper, noted hereinabove.

Preferably, the denier and strength of the capillary channel fibers will be chosen such that the batt of fibers will have a ratio of wet:dry caliper of at least about 80%, more preferably at least about 90%. This ensures that the batt will retain its soft and form-fitting qualities in use. (All percentages, ratios and proportions set our in this specification are by weight, unless otherwise specified.)

Stated otherwise, for a typical sanitary napkin, approximately 1.5 g of curled capillary channel fibers will provide a rectangular batt having a surface area of about 160 $cm^2$. Such a batt could be suitable for use as layer which might be termed a "secondary topsheet", underlying the initial fluid-receiving topsheet of the type disclosed above.

(4) Use of Capillary Channel Fiber Batts in Absorbent Articles

The capillary channel fiber batts will have some amount of holding capacity for fluids, such as menstrual fluids. Accordingly, the capillary channel fiber batts can, if desired, comprise the entire absorbent core of pantiliners, for example.

However, for most uses, the capillary channel fiber batts will be used in conjunction with an absorbent core, and the core will serve as a reservoir for fluids which are transferred from the capillary channel fiber pad into the core. Such cores may, for purposes of the following discussion, comprise an air-laid felt of cellulosic fibers, or mixtures of cellulosic fibers with absorbent gelling materials.

Due to the extremely fine structure of the cellulosic fibers in such absorbent cores, the cores exhibit high suctional forces which tend to draw away fluids from the capillary channel fibers and into the core for ultimate storage. This is precisely the intended effect. Thus, for a sanitary napkin, typical cores which comprise from about 1 g to about 5 g of multiple cellulosic fibers and, optionally, from about 0.5 g to about 1.5 g of absorbent gelling material, are overlaid with a capillary channel fiber batt prepared as described above. As fluid proceeds into the article, it encounters the capillary channel fiber network, which distributes the fluid and then surrenders it to the underlying absorbent core, thereby at least partially "renewing" the capillary channel fiber network for the next infusion of fluid.

In one preferred mode, the capillary channel fiber batt may be used as a "secondary" topsheet under a porous (preferably formed-film) topsheet. Thus, the capillary channel fibers draw fluid through the topsheet, thereby leaving the topsheet with a fresh, dry appearance and feel, then surrender the fluid to the underlying absorbent core, and are thus able to continue the process until the core is saturated.

The liquid handling characteristics of the components of such absorbent articles are described in U.S. application Ser. No. 07/915,286, entitled "Absorbent Articles, Especially Catamenials, Having Improved Fluid Directionality" filed in the names of H. A. Thompson, et al. on the same date as the present application.

(5) Contact Between Topsheet and Capillary Channel Fibers

The batt 44 of capillary channel fibers is preferably kept in close contact with the overlying topsheet 38. This can be achieved by a number of suitable mechanisms. These include, but are not limited to bonding the batt 44 to the topsheet 38 by adhesives, ultrasonics, and the like, or by tensional forces. The contact between the topsheet 38 and the capillary channel fibers may be close enough so that some of the tufts of the capillary channel fibers 90 extend into the orifices of the topsheet.

Thus, in a highly preferred mode there is an interconnecting network between topsheet, thence into the capillary channel fiber pad, and thence into the underlying absorbent core, whereby fluid efficiently proceeds through the topsheet 38, along and through the capillary channel bun 44, and into the absorbent core 42. This interconnection is preferably maintained even in the face of in-use stresses such as moisture, mechanical shear, and pressure-relaxation associated with physical movements of the wearer.

If an adhesive attachment is used, several factors should be kept in mind. The amounts of adhesive used and the pattern in which it is laid-down should minimize the sticking of the absorbent article to the user's body. The adhesive should be nonirritating to the skin and toxicologically-acceptable. The adhesive should maintain its bonding properties when moisture is not present, i.e., when the article is being manufactured, and, most preferably, when moisture is present, i.e., when the absorbent article is being used. Thus, it is preferred that the adhesive be insoluble in body fluids.

The adhesive should also bond both to the material used to manufacture the topsheet and to the material used to manufacture the capillary channel fibers. If the topsheet or the fibers are surface-treated, e.g., in a hydrophilization process, the nature of the surface treatment will have to be considered when selecting the adhesive.

Typical adhesives useful herein include materials selected from latex adhesives and hot melt adhesives. Suitable adhesives are available from Findley Adhesives, Inc., as hot melt adhesive 4031, and latex 8085. The type of adhesive can vary somewhat depending on the type of hydrophilic finish present on the capillary channel fibers.

Suitable finishes include Eastman's LK 5483, LK 5563, and most preferably Eastman's LK 5570, as well as the polymer available as MILEASE T, which is well-known in the detergency arts (see, for example, U.S. Pat. No. 4,132, 680) as a fiber-coating soil release polymer, and which is available from ICI Americas.

Figure 13:
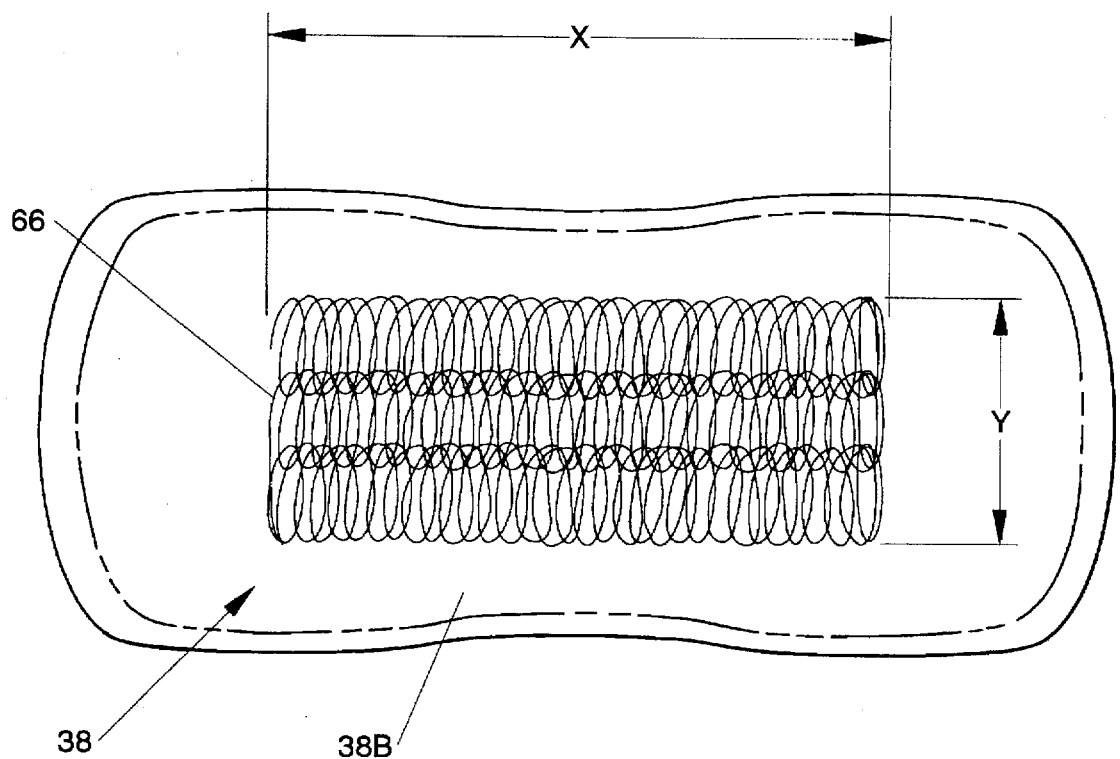
FIG. 13 shows the underside of a topsheet and one preferred multi-spiral pattern of glue lines used to affix the topsheet to the layer of capillary channel fibers.

The adhesive can be laid down in a random pattern, however, it is preferred that a spiral, or multiple spiral, pattern, such as the one illustrated in FIG. 13, be used. The lines of adhesive are applied in the spiral pattern using 0.2 mm nozzle, but application using nozzles at least as large as 0.6 mm is satisfactory. The amounts of adhesive employed will vary, but typically range from about 0.05 g for a 2 in.×5 in. spiral pattern to about 0.07 g for a 2 in.×7 in. spiral pattern, using a hot melt adhesive. For a latex adhesive, from about 0.1 g to about 0.15 g for a 2 in.×5 in. pattern will suffice.

The adhesives may be applied in an open pattern network of filaments of adhesive as is disclosed in U.S. Pat. No. 4,573,986 which issued to Minetola, et al. on Mar. 4, 1986. Some suitable attachment means that utilize an open pattern network of filaments comprising several lines of adhesive filaments swirled into a spiral pattern are illustrated by the apparatus and methods disclosed in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989.

Close contact between the topsheet and the underlying layer of capillary channel fibers can be further improved by applying pressure during the gluing process and/or by "combing" the uppermost capillary channel fibers in the layer to provide individual fiber protrusions which give better contact with the adhesive.

(6) Contact Between the Capillary Channel Fibers and the Absorbent Core

It is preferable that there also be close contact between the capillary channel fibers 90 and the absorbent core 42 in order to efficiently transfer liquids to the absorbent core 42.

This close contact can also be achieved in a number of ways. These include, but are not limited to, the use of adhesives, ultrasonic bonds, by tensional forces, by providing a roughened surface of the absorbent core, or by needle-punching, or otherwise inserting some of the capillary channel fibers into the absorbent core.

Preferably, as shown in FIG. 7, the base of the tuft 44 of capillary channel fibers is slipped into a slit in the top of the core/nonwoven sheet sandwich.

The tuft 44 of capillary channel fibers has two end extensions designated 94. The end extensions 94 extend outward at the base of the tuft 44 in opposite directions. The end extensions 94 preferably extend along the longitudinal centerline L. The end extensions 94 are in fluid (i.e., liquid) transporting contact with the upper portion of the tuft 44 of capillary channel fibers. The end extensions 94 are also in fluid transporting contact with the absorbent core laminate.

The tufted bun 44 of capillary channel fibers provides the sanitary napkin 20 with a component having liquid transport, and preferably liquid acquisition/distribution capabilities. The capillary channel fibers will typically be primarily used to transport liquids deposited on the bun 44 due to the capillary gradient described above, rather than to absorb the same. The bun 44 of capillary channel fibers may, therefore, also be referred to as a "transport component", a "liquid acquisition/distribution component", or by some other suitable name that describes its function. This liquid acquisition/distribution component 44 has several key features.

The liquid acquisition/distribution component 44 comprises an upper portion 47 that extends above the main absorbent component of the sanitary napkin, the absorbent core 42. This upper portion 47 of the acquisition/distribution component 44 can be positioned in close contact with the wearer' body. Even more advantageously, the upper portion 47 of the liquid acquisition/distribution component 44 can be of such a size and shape that it can fit at least partially within the space between the wearer's labia. This allows it to more readily intercept exudates that leave the wearer's body.

The end extensions 94 of the bun 44 provide a liquid acquisition/distribution component with conduits for transporting liquids directly to the absorbent core 42. Even more preferably, the end extensions 94 are capable of transporting liquids to the interior of the absorbent core 42. This provides the sanitary napkin 20 with another advantage.

Generally, when exudates are simply deposited on top of an absorbent component, such as the absorbent core 42, they can be absorbed readily along the top surface of the absorbent component. However, liquids tend to remain in and fill the upper parts of the core first. This blocks the transportation of exudates to the lower regions of the core. The end extensions 94 reduce the potential for this problem to occur. The end extensions 94 eliminate the need for liquids to travel through one part of an absorbent storage component to get to the place where available absorbent capacity exists.

The construction of the sanitary napkin 20 described above is only one possible arrangement of the acquisition/distribution component, however. Many other suitable arrangements of components are possible if the principles discussed above are followed. For instance, the end extensions 94 (or other portions of the capillary channel fiber bun) could be placed in contact with the absorbent core 42 in a number of different ways.

The following is a non-limiting list of possible relationships between the end extensions 94 and the absorbent core 42. They are generally arranged from more to less preferred. The end extensions could be: (1) surrounded by the other components of the absorbent core (those with higher capillarity) such as in the pleated core embodiment described above; (2) commingled or integrated into the other components; (3) placed between two or more layers of the other components, such as described immediately above; (4) placed under at least one other layer; or, (5) placed on top of the other components.

The sanitary napkin 20 may have other types of acquisition/distribution components or layer(s) positioned between the topsheet and the absorbent core. Preferably, the embodiment shown in FIG. 7 has an additional acquisition layer (or "secondary topsheet") 46 positioned between the topsheet 38 and the absorbent core 42. Such an additional acquisition layer could be used to distribute body exudates that are deposited longitudinally or laterally outside of the bun 44 of capillary channel fibers to the absorbent core 42.

These other types of acquisition/distribution components, the methods of securing the same in absorbent articles, and the functions served by the same are described in U.S. Pat. Nos. 4,950,264 and 5,009,653 issued to Osborn, and in U.S. patent application Ser. No. 07/810,774, "Absorbent Article Having Fused Layers", filed Dec. 17, 1991 in the names of Cree, et al.

The acquisition/distribution component or components may be comprised of other types of material (instead of capillary channel fibers). These include, but are not limited to nonwoven or woven webs of synthetic fibers including polyester, polypropylene, or polyethylene; natural fibers including cotton or cellulose; blends of such fibers; or any equivalent materials or combinations of materials.

E. Assembly of the Components of the Sanitary Napkin

The preferred sanitary napkin embodiment shown in FIG. 1 has its components assembled with several different types of attachment mechanisms. These attachment mechanisms (or attachment means) will be discussed with reference to FIG. 7. The discussion will proceed from a description of the inside of the sanitary napkin 20 to the outside.

For the purposes of this discussion, the absorbent core 42 will comprise the cross-linked cellulosic laminate described above.

The absorbent core 42, as noted above, is preferably sandwiched between the nonwoven secondary topsheet 44 and the nonwoven layer 48 to form a "core/nonwoven sheet sandwich" 51. The components of the core/nonwoven sheet sandwich 51 can be secured together in any suitable manner. The components in the embodiment shown in FIG. 7 are secured together by stitching lines 70.

The stitching of these components serves several purposes. These include, but are not limited to the following. The stitching holds the components of the core/nonwoven sheet sandwich 51 together. Stitching is a preferred mechanism for holding these components together because it is a very permanent method of bonding such components together. The stitching also holds up well in the presence of liquids.

The stitching also enhances the transfer of liquids between the layers of the core/nonwoven sheet sandwich. The stitching secures the components of the core/nonwoven sheet sandwich together in such a manner that the components are held in sustained close contact with each other. As discussed above, this contacting relationship is one of the features needed for the transportation of liquids down into underlying components.

The stitching need not be limited to the core/nonwoven sheet sandwich, however. Stitching can be used to secure together any of the components of the sanitary napkin located between (and including) the topsheet 38 and the backsheet 40.

The topsheet 38 is bonded to the tuft of capillary channel fibers by a topsheet bonding adhesive 66. The preferred method of bonding the topsheet is described in greater detail in Section 3D(5) above, and in the following Examples.

The backsheet 40 is bonded to the garment side of the core/nonwoven sheet laminate 51. This is accomplished in the embodiment shown in FIG. 7 by two strips of construction adhesive 68.

The topsheet 38 and backsheet 40 are then secured together. The topsheet 38 and backsheet 40 have length and width dimensions that are greater than those of the absorbent core 42. The topsheet 38 and backsheet 40, therefore, extend beyond the edges of the absorbent core 42 to form at least part of the periphery 26 of the sanitary napkin.

The topsheet 38 and backsheet 40 are secured to each other around at least part of the periphery 26 of the sanitary napkin 20 by a perimeter heat seal. The formation of this perimeter heat seal 71 is described in greater detail in Section 4 below which describes methods of making the sanitary napkin 20 of the present invention.

The topsheet, the backsheet, the absorbent core, and any other components, may be assembled in a variety of well known configurations (including so called "tube" products or side flap products). Several other suitable sanitary napkin configurations are described generally in the aforementioned U.S. Pat. Nos. 4,950,264 and 5,009,653 issued to Osborn; U.S. Pat. No. 4,425,130, "Compound Sanitary Napkin" issued to DesMarais on Jan. 10, 1984; U.S. Pat. No. 4,321, 924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987.

The description of the mechanisms for securing the various components of the sanitary napkin 20 is but one preferred way of constructing the sanitary napkin. Any of the components of the sanitary napkin 20 can be secured together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, or by any other means known in the art.

F. Fasteners for Attaching the Sanitary Napkin to the Wearer's Panties

In use, the sanitary napkin 20 can be held in place in the wearer's undergarments by any suitable means. Preferably, the sanitary napkin 20 is placed in the user's panty and secured thereto by a fastener such as an adhesive located on the garment surface 40B of the backsheet 40. The adhesive provides a means for securing the sanitary napkin in the crotch portion of the panty.

FIG. 7 shows a particularly preferred adhesive pattern or configuration. The adhesive is arranged in the form of four generally rectangular strips or patches of adhesive. These patches are arranged so that the overall adhesive pattern resembles a letter "X" with the center of the "X" missing and each of the patches running in a direction from the intersection of the longitudinal and transverse centerlines, C, to one of the corners 27 of the sanitary napkin.

The adhesive pattern shown in FIG. 7 is particularly preferred on embodiments having a hump 72. The absence of adhesive in the center permits the portion of the sanitary napkin with the hump 72 to decouple or separate from the wearer's undergarments. This provides for more sustained contact of the hump 72 with the wearer's body when the sanitary napkin 20 is worn.

The ends of the adhesive patches are preferably located as close as possible to the transverse end edges 24 of the sanitary napkin 20. This principle of adhesive configuration is discussed in PCT International patent Publication No. WO 92/04000 entitled "Shape and Adhesive Fastening Means for an Absorbent Article" published in the name of Papa, et al. on Mar. 19, 1992. Other aspects (no adhesive in the central region 32) operate on principles peculiar to the configuration of the sanitary napkin of the present invention.

Other suitable adhesive configurations are also possible. For example, the adhesive could be applied in an inverted V-shape, or chevron pattern, in each end region 28 and 30 of the sanitary napkin 20.

Any adhesive or glue used in the art for such purposes can be used, with pressure-sensitive adhesives being preferred. Suitable adhesives are Century A-305-IV manufactured by the Century Adhesives Corporation, Instant Lock 34-2823 manufactured by the National Starch Company, and 3 Sigma 3153 manufactured by 3 Sigma. Suitable adhesive fasteners are also described in U.S. Pat. No. 4,917,697.

Before the sanitary napkin 20 is placed in use, the pressure-sensitive adhesive is typically covered with a removable cover strip or release liner 52 in order to keep the adhesive from sticking to a surface other than the crotch portion of the panty prior to use. Suitable release liners are also described in the above-referenced U.S. Pat. No. 4,917, 697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation.

The sanitary napkin 20 of the present invention is used by removing the release liner 52 and thereafter placing the sanitary napkin in a panty so that the adhesive 50 contacts the panty. The adhesive maintains the sanitary napkin in its position within the panty during use.

In still other embodiments, other types of fasteners can be used instead of, or in addition to adhesives. These other types of fasteners are preferably arranged in patterns similar to those described above.

Such fasteners include, but are not limited to conventional VELCRO hook material, the fasteners described in: U.S.

Pat. No. 4,946,527 issued to Battrell on Aug. 7, 1990, U.S. Pat. Nos. 5,058,247 and 5,116,563 issued to Thomas, et al. on Oct. 22, 1991 and May 26, 1992, respectively; and EPO patent application publication No. 0 381 087 published Aug. 8, 1990; or, the high coefficient of friction foams and other high coefficient of friction materials such as those described in U.S. Pat. No. 4,166,464 issued to Korpman, U.S. Pat. No. 4,834,739 issued to Linker, III, et al., and U.S. Pat. No. 5,011,480 issued to Gossens, et al.

G. Optional Features

The sanitary napkin 20 may also be provided with two flaps 56, each of which are adjacent to and extend laterally from the side edge of the absorbent core. The flaps 56 are configured to drape over the edges of the wearer's panties in the crotch region so that the flaps 56 are disposed between the edges of the wearer's panties and the thighs.

The flaps 56 serve at least two purposes. First, the flaps 56 help serve to prevent soiling of the wearer's body and panties by menstrual fluid, preferably by forming a double wall barrier along the edges of the panty. Second, the flaps 56 are preferably provided with attachment means on their garment surface so that the flaps 56 can be folded back under the panty and attached to the garment facing side of the panty. In this way, the flaps 56 serve to keep the sanitary napkin properly positioned in the panty.

The flaps 56 can be constructed of various materials including materials similar to the topsheet, backsheet, tissue, or combination of these materials. Further, the flaps 56 may be a separate element attached to the main body portion 21 of the napkin or can comprise extensions of the topsheet 38 and backsheet 40 (i.e., unitary).

A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986.

Alternatively, as shown in FIG. 1, the flaps may not be as large as some of the flaps described in the foregoing references. Such flaps could comprise an unbonded nonwoven facing material laminated to an elastomeric adhesive. The elastomeric adhesive preferably liquid impervious. At least a portion of the laminate preferably exhibits a low modulus of elasticity and does not fully recover after elongation.

The portion of the laminate that does not fully recover after elongation provides the advantage that it deforms easily when the pad is placed in the wearer's panties and the panties are pulled on. This embodiment assist the wearer in wrapping the flaps around the portions of the panty containing the leg elastics.

For instance, the portion of the laminate that does not fully recover after elongation could comprise zones on the ends of the flaps comprised of only the nonwoven material. When the flaps are wrapped around the portion of the panties containing the leg elastics, these zones will tend to permanently deform. The permanent deformation of the material in these zones will help hold the flap wrapped around the panty elastics.

The sanitary napkin may also be constructed as described below by differentially stretching a component (i.e. just in the middle) to provide specific types of curvature. The sanitary napkin may be constructed with a variety of features including 1) partial wrapping of the core or other components with the topsheet, 2) partial wrapping of the core or other components with the backsheet (features (1) and (2) can comprise the so-called "tube" products that have components that are at least partially wrapped in other components as opposed to being laminated together to form a product having a sandwich-like construction), 3) rolled edges (for example, the edges of the sanitary napkin could be curled or formed into a scroll-like structure for added comfort), 4) edges of pad covered with soft material (functional and/or aesthetic) (for example, the material that extends outward to form the extensions of the topsheet 54 in FIG. 7 are preferably wrapped around the longitudinal side edges of the other components and secured to the backsheet 40), and 5) edges of sanitary napkin which have specific levels of stiffness for control.

In addition, the sanitary napkin described herein can employ slitted or partially slitted absorbent cores, together with curled capillary channel fibers and other extensible components which, together, provide a degree of extensibility (on the order of 15%–40%) to the article. This extensibility may provide better in-use fit and comfort. In a particularly preferred alternative embodiment, the sanitary napkin 20 is comprised of components that are extensible (preferably, capable of stretching), particularly in the longitudinal direction when the sanitary napkin is worn.

In one preferred embodiment of the present invention, the topsheet 38 is made in accordance with U.S. Pat. No. 4,463,045 and ring rolled to provide it with a degree of longitudinal extensibility. The fold lines in the corrugations of a ring rolled topsheet 38 run in the transverse direction so the topsheet 38 is longitudinally extensible.

The absorbent core 42 is a laminate as described above which is slitted or partially slitted for longitudinal extensibility. The absorbent core 42 could be slit in the end regions 28 and 30, but not in the central region 32. Other types of slit absorbent materials are described in European Patent Application Publication Number 0 293 208 B1 published by Lion Corporation on Jul. 24, 1991.

A particularly preferred extensible backsheet 40 is an extended adhesive film known as Formula #198-388 manufactured by the Findley Adhesives Company of Wauwatosa, Wis. The nonwoven layers 46 and 48 can be creped to provide them with extensibility. The sanitary napkin 20 is preferably sealed to prevent the wicking and expulsion of liquid or liquid-containing superabsorbent material from the napkin when it is extended.

The fastener can comprise a fastener, such as adhesive patches that are extensible, inextensible, or some portions of the fastener can be extensible and some inextensible. The adhesive fastener is protected with a wrapper that provides both an individually packaged sanitary napkin and a container for disposing the sanitary napkin after use, such as is described in U.S. Pat. No. 4,556,146 issued to Swanson, et al. on Dec. 3, 1985.

Suitable extensible absorbent articles are described in a concurrently-filed U.S. Patent Application entitled "Stretchable Absorbent Articles" filed in the name of Osborn, et al.

The capillary channel fibers can also be conveniently formed into a stable sheet for ease-of-manufacture into absorbent articles by means of various bonding processes. For example, about 20%–30% by weight of polyester thermoplastic fibers (e.g., KODEL 410) can be commingled with the capillary channel fibers and the resulting fibrous sheet subjected to direct thermal or through-air heating.

The refined curled cellulosic fibers can be conveniently formed into a stable sheet for ease-of-manufacture into absorbent articles by means of various bonding processes. For example, about 7%–15% by weight of polyester thermoplastic fibers (e.g., KODEL 410) can be commingled with the refined curled cellulosic fibers and the resulting fibrous sheet subjected to through-air heating or ultrasonic bonding.

Incorporation of thermoplastic fibers into the capillary channel fiber layer or into the absorbent core layer, or both, offers advantages in addition to the sheet stability noted above. In particular, having the thermoplastic fibers present in the core, or in the capillary channel fiber layer, or both, allows the manufacturer to provide a seal at the periphery (at least in the crotch region) of, for example, a sanitary napkin or pantiliner, said seal providing a means whereby fluid overflow around the edges of the article is impeded, or stopped altogether.

In an alternate mode, the thermoplastic topsheet, the core containing the thermoplastic fibers and the backsheet can all be bonded together at or near the periphery by means of ultrasonic bonding. In still another mode, the layer of capillary channel fibers containing the admixed thermoplastic fibers can likewise be bonded to the core (and also to the topsheet, if desired). In still another mode, the presence of thermoplastic fibers in the core and/or in the layer of capillary fibers allows for spot bonding at various points across the article, thereby providing additional integrity when the article becomes wet.

The various features of the present invention are described and claimed in the following pending U.S. Patent Applications which were filed on the same date as the present application U.S. patent application Ser. No. 07/915,285, entitled "Curved, Shaped Absorbent Article" filed in the name of Theresa L. Johnson, et al.; U.S. patent application Ser. No. 07/915,201, entitled "Absorbent Article Fastener Pattern" filed in the name of Robb E. Olsen, et al.; and, U.S. patent application Ser. No. 07/915,134, entitled "Method of Making Curved, Shaped Absorbent Article" filed in the name of Letha M. Hines, et al.

In still other alternative embodiments, components or regions of the sanitary napkin may be further structurally modified by folding, bending, corrugating, stacking of layers and affixing layers to each other. The modifications may be made by including one or more of the structures described in European Patent Application Publication Nos. 0 335 252 and 0 335 253 published in the name of Buell on Oct. 4, 1989, in PCT Patent Application Publication No. WO 92/07535 published in the name of Visscher, et al., and in U.S. patent application Ser. No. 07/874,872 entitled "Generally Thin, Flexible Sanitary Napkin Having Stiffened Center" filed in the name of Osborn on Apr. 28, 1992.

While several preferred sanitary napkin embodiments have been described, numerous other sanitary napkin embodiments are disclosed in the literature. These could be provided in the curved, shaped configuration of the present invention. Some of such sanitary napkins are described in U.S. patent application Ser. No. 07/605,583 filed Oct. 29, 1990 in the name of Visscher, et al., U.S. Pat. Nos. 5,009,653 and 4,950,264, issued to Osborn on Apr. 23, 1991 and Aug. 21, 1990, respectively. U.S. Pat. No. 4,940,462, issued to Salerno on Jul. 10, 1990, U.S. Pat. No. 4,917,697 issued to Osborn, III, et al. on Apr. 17, 1990, U.S. Pat. No. 4,911,701 issued to Mavinkurve on Mar. 27, 1990, U.S. Pat. No. 4,900,320, issued to McCoy on Feb. 13, 1990, U.S. Pat. No. 4,687,478 issued to Van Tilburg on Aug. 18, 1987, U.S. Pat. No. 4,608,047 issued to Mattingly on Aug. 26, 1986, U.S. Pat. No. 4,589,876 issued to Van Tilburg on May 20, 1986, U.S. Pat. No. 4,285,343 issued to McNair on Aug. 25, 1981, U.S. Pat. No. 3,397,697 issued to Rickard on Aug. 20, 1968, and U.S. Pat. No. 2,787,241 issued to Clark on Apr. 2, 1957.

The terms "panty liner" or "pantiliner" refer to absorbent articles that are less bulky than sanitary napkins which are generally worn by women between their menstrual periods. Suitable absorbent articles in the form of pantiliners which could be provided in the curved, shaped configuration of the present invention are disclosed in U.S. Pat. No. 4,738,676 entitled "Pantiliner" issued to Osborn on Apr. 19, 1988.

The term "incontinent article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided in the curved, shaped configuration described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991.

The focus of the present invention is on absorbent articles that are intended to be worn in the crotch region of the wearer's undergarments. However, the features of the present invention could also be used in absorbent articles such as diapers. Diapers are absorbent articles worn by infants and incontinent persons that are fastened about the waist of the wearer.

Suitable diapers that can be provided in the curved, shaped configuration of the present invention are disclosed in U.S. Pat. No. 3,860,003 issued to Buell on Jan. 14, 1975, and U.S. patent application Ser. No. 07/715,152 filed in the name of Buell, et al. on Jun. 13, 1991.

4. Method of Making the Absorbent Article

A. In General

The three-dimensional shaping of the sanitary napkin 20 involves providing the sanitary napkin with lengthwise and transverse curvature.

The concept of providing an article, such as the sanitary napkin 20, with curvature can be thought of in the broadest sense, as making the dimensions of one face of the article greater than the dimensions of the other face. For instance, if the length of one face of the article is greater than the length of the other face, the article will curve inward along the shorter face of the article.

This shaping of the sanitary napkin 20 can be achieved in at least three basic ways.

The first way of shaping the sanitary napkin 20 involves securing at least two components together. The components typically have different dimensions (i.e., one is larger than the other in at least one dimension). The components are preferably secured together in such a way that their ends terminate at the same point when the components are secured. This first way of shaping the sanitary napkin generally involves securing the components together when they are placed on a curved surface, such as in a curved form.

The second basic way of shaping the sanitary napkin 20 involves foreshortening at least a portion of one of the components of the sanitary napkin and securing it to one of the other components. The second way requires that at least one of the components (for example the first component) be both extensible and contractible. In the second way of shaping the sanitary napkin, the first component is stretched, secured to the second component, and allowed to contract. The sanitary napkin 20 formed in this manner generally curves inward along the face nearest to the first component.

The third way of the curving the sanitary napkin 20 is by some suitable process which results in lengthening one of the faces of the sanitary napkin 20. This can, for example, be done by stretching or heating and stretching the backsheet 40 of the sanitary napkin 20. This will result in a sanitary napkin that is curved inward along the topsheet 38.

B. Methods Which Involve Securing the Components When Placed on Curved Surfaces

The first method of making a sanitary napkin in a curved configuration, as noted above, generally involves placing the components for the sanitary napkin in a curved form such as a trough and securing the components together in the desired shape. This can be done by hand, or by machine.

(1) Making The Sanitary Napkin By Hand

Figure 14:
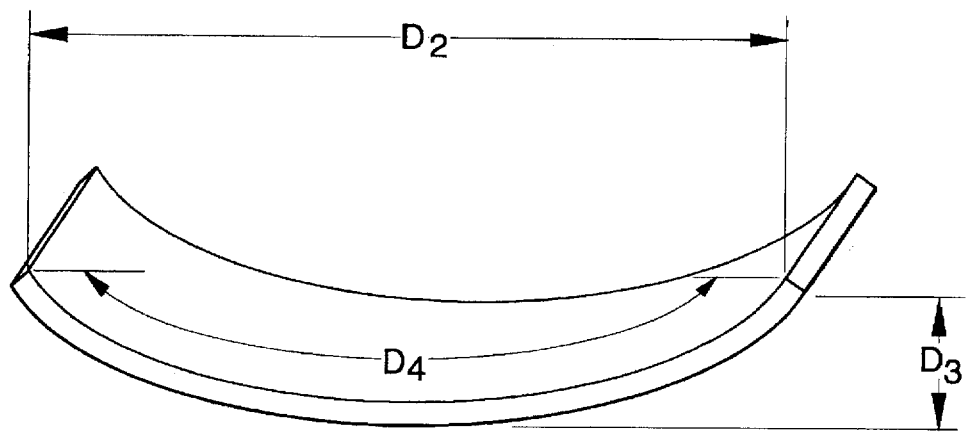
FIG. 14 is a perspective view of a form in which the components of the sanitary napkin could be assembled by hand.
Figure 15:
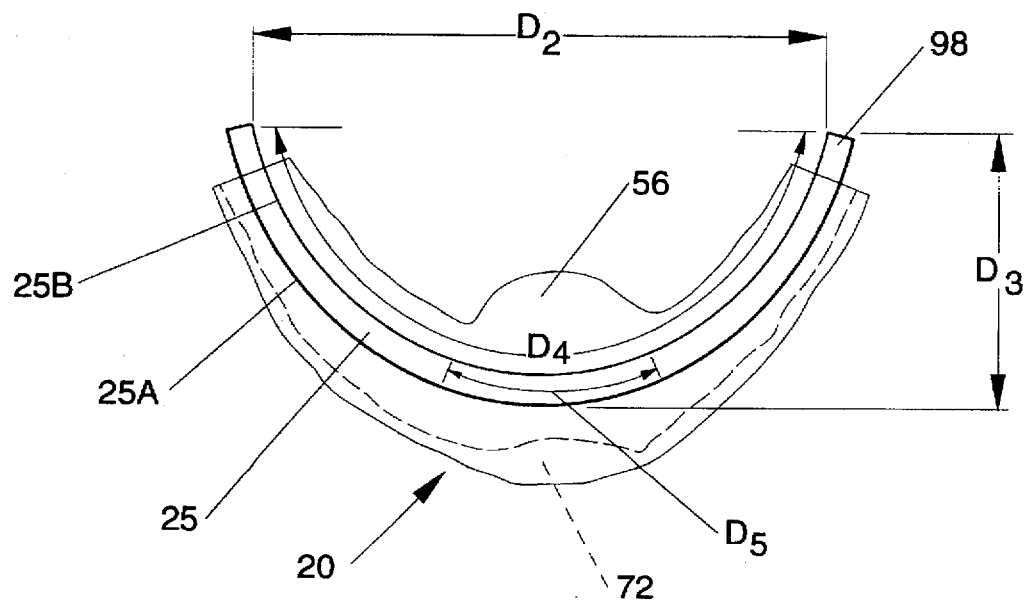
FIG. 15 is a perspective view of a form in which the components of the sanitary napkin could be sealed by hand.

FIGS. 14 and 15 show preferred curved forms for use in making the sanitary napkin 20.

The curved form shown in FIG. 14 is used for assembling the components of the sanitary napkin 20. The form shown in FIG. 14 has a length $D_2$ of about 7¾ inches (about 20 cm.). When this form is placed on a flat surface, it has a height $D_3$ above the plane of the flat surface of about 3 inches (about 7.5 cm.). The form has an arc length $D_4$ measured along its curved inside surface of about 10¼ inches (about 26 cm.).

The curved form shown in FIG. 15 is used for sealing the longitudinal side margins 25 of the assembled sanitary napkin components. The form shown in FIG. 15 has a length $D_2$ of about 6 inches (about 15 cm.). When this form is placed on a flat surface, it has a height $D_3$ above the plane of the flat surface of about 3¼ inches (about 8 cm.). This form has an arc length $D_4$ measured along its curved inside surface of about 9 inches (about 23 cm.). The length of the seal area $D_5$ along this arc is about 3 inches (about 7.5 cm.).

The sanitary napkin 20 is assembled by hand in the following manner. For simplicity, the assembly is described in terms of one possible method. The steps described below can be carried out in many other orders. There are also numerous other ways to assemble the sanitary napkin. All such alternatives are within the scope of the present invention.

The components for the absorbent core 42 are obtained. The absorbent core 42 used is the preferred laminate described above of two layers of cross-linked cellulose fibers 43 and 45 with absorbent gelling material particles 41 therebetween.

The absorbent gelling material particles 41 are placed on top of the web (or portion thereof) that will form the bottom layer 45 of cross-linked cellulose fibers.

The capillary channel fibers 90 are obtained. The capillary channel fibers 90 are preferably substantially curled. Suitable capillary channel fibers are those designated SW173 available from the Eastman Chemical Company. The SW173 fibers comprise a carded staple sliver which has been stuffer box crimped to 7.8 crimps per inch and have an H-shaped cross-section with a channel width of 38 microns and a channel depth of 19 microns. The capillary channel fibers are preferably 6 in. long; 0.75 g. fibers are used.

The capillary channel fibers 90 are provided in the form of a layer that is gathered in its center to form an oval tuft having the dimensions described above. The longitudinal ends of the layer of capillary channel fibers are formed into end extensions 94.

The bun of capillary channel fibers 44 is placed on top of the absorbent gelling material 41. The bun 44 is oriented so that the extensions 94 from the base 74 of the same will extend along the longitudinal centerline L of the completely assembled sanitary napkin.

The web of cross-linked cellulose fibers (or portion thereof) that will form the upper layer 43 of the core 42 is provided with a longitudinal slit. The slit is provided in the portion of the upper layer 43 that will lie in the central region 32 of the completely assembled sanitary napkin. The slitted web aids in retaining the tufted bundle of fibers in its tufted configuration. In other embodiments, other suitable mechanisms can be used to retain the bundle of fibers in its tufted configuration.

The upper layer 43 of the core 42 is placed on top of the bun 44 of capillary channel fibers and layer of particles of absorbent gelling material. The upper portion 47 of the bun 44 of capillary channel fibers is pulled up through the slit to form a tuft. This leaves the upper portion 47 of the bun 44 exposed. The extensions 94 remain in place within the absorbent core laminate on top of the layer of absorbent gelling material 41. This forms an absorbent core pre-assembly.

The secondary topsheet 46 material is provided. The layer of material comprising the secondary topsheet 46 is also provided with a longitudinal slit. The secondary topsheet 46 is placed on the body-facing side of the absorbent core pre-assembly. The upper portion 47 of the tuft 44 of capillary channel fibers is pulled through the slit in the secondary topsheet 46. The nonwoven layer 48 is positioned on the garment-facing side of the core pre-assembly. This forms the absorbent core/nonwoven sheet laminate 51.

The components of the absorbent core/nonwoven sheet laminate 51 are then stitched together along stitching lines 70 such as those shown in FIG. 7.

The absorbent core/nonwoven sheet laminate 51 and the other components of the sanitary napkin are then assembled in the curved form shown in FIG. 14. The backsheet 40 material is first placed in the curved form. The two strips of construction adhesive 68 are placed on the backsheet 40 near the longitudinal side edges of the backsheet material. The absorbent core/nonwoven sheet laminate 51 is placed in the form on top of the construction adhesive 68 located on the backsheet 40 material.

The topsheet 38 is sprayed with the topsheet bonding adhesive 66 on its garment-facing side 38B. Preferably, the adhesive 66 is applied in a spiral pattern such as that shown in FIG. 13. The topsheet 38 is shown in FIG. 13 in its final cut configuration.

(The topsheet 38, however, will often be in an untrimmed or partially untrimmed configuration with excess material around the periphery of the topsheet 38. This excess material will typically be removed after the portions of the components of the sanitary napkin that will form the longitudinal side margins 25 are sealed.)

The topsheet 38 is then placed on top of the absorbent core/nonwoven sheet laminate 51 (with the tuft 44 still protruding from the core/nonwoven sheet laminate 51). This forms a pre-assembled sanitary napkin. The pre-assembled sanitary napkin is then ready to be sealed in a curved configuration.

The pre-assembled sanitary napkin is taken out of the curved form shown in FIG. 14. The longitudinal side margins 25 of the pre-assembled sanitary napkin are sealed as follows.

The sanitary napkin components may be maintained in a curved configuration in some suitable manner. Preferably, the components are maintained in a curved configuration by using the curved form shown in FIG. 15. The curved form shown in FIG. 15 is preferably turned on its side edge 98. The pre-assembled sanitary napkin is placed on the outside surface of the curved form. The pre-assembled sanitary napkin is placed so the longitudinal side margin 25 to be sealed is positioned on the side edge 98 of the curved form as shown in FIG. 15.

The side edge 98 of the curved form shown in FIG. 15 is preferably oriented approximately perpendicular to the inside surface of the form.

This allows the seal to be formed when the longitudinal side margins 25 of the pre-assembled sanitary napkin are placed on a curved surface and bent out of the plane of the adjacent portions of the topsheet 38 toward the surface of the pre-assembled sanitary napkin that will form the body surface 20A of the sanitary napkin when they are sealed. Specifically, the longitudinal side margins 25 are bent out of the plane of the topsheet at an angle of approximately 90° toward the topsheet 38.

The bending of the longitudinal side margins 25 out of the plane of the topsheet 38 before sealing aids in creating the aforementioned overlapping by foreshortening the distal edges 25B of the longitudinal side margins 25. It also provides the sanitary napkin with cross direction curvature, and assists the longitudinal side margins 25 in standing up.

The longitudinal side margins 25 do not have to be bent inward at a 90° angle, however. The longitudinal side margins 25 can be bent at any suitable angle, and still provide some of the benefits described herein. In other alternative embodiments, the longitudinal side margins 25 may not be bent at all.

The longitudinal side margins 25 are then sealed. In the preferred process described herein, the longitudinal side margins 25 of the sanitary napkin 20 are sealed by a heated element. The heated element is essentially used to "iron" the longitudinal side margins in a configuration where the distal edges 25B of the side margins 25 are in a (preferably curved) foreshortened state.

The heated element can be any suitable type of heating device, such as a heated plate, a bar sealer, a spatula type sealer, etc.

In other embodiments of this process, the longitudinal side margins 25 can be sealed in a curved configuration in alternative manners. Any method of maintaining the longitudinal side margins 25 in a configuration with the distal edges 25B of the same in a foreshortened condition can be used. Such methods include, but are not limited to crimping the longitudinal side margins 25, as well as affixing a piece of tape to the longitudinal side margins 25 can be used.

The effect of sealing the longitudinal side margins 25 in such a manner is that a multiplicity of very small areas or portions along the longitudinal side margins 25 of the sanitary napkin overlap before the longitudinal side margins 25 are sealed (i.e., it creates many barely visible mini-tucks). This provides the longitudinal side margins 25 (and, thus, the sanitary napkin 20) with curvature.

It is also within the scope of the present invention for the seal to be formed when the longitudinal side margin 25 of the pre-assembled sanitary napkin is placed in or on some other surface. For instance, the sanitary napkin could be assembled and sealed in a single form.

The subsequent steps of the assembly of the sanitary napkin, such as sealing the remainder of the perimeter of the sanitary napkin (or other portions of the components), and cutting the excess material outboard of the perimeter seal can be performed in any suitable manner.

For instance, the remainder of the perimeter of the sanitary napkin can be sealed while the sanitary napkin is in a curved configuration. Alternatively, the remainder of the perimeter could be sealed when the pre-assembled sanitary napkin is in a less curved configuration, or even a flattened configuration to form a more gradually curved product and/or a product having differential curvature. (For example, the end regions 28 and 30 could be flattened and sealed to provide end regions that are less curved than the central region 32.)

(2) Making The Sanitary Napkin By Machine

Figure 16:
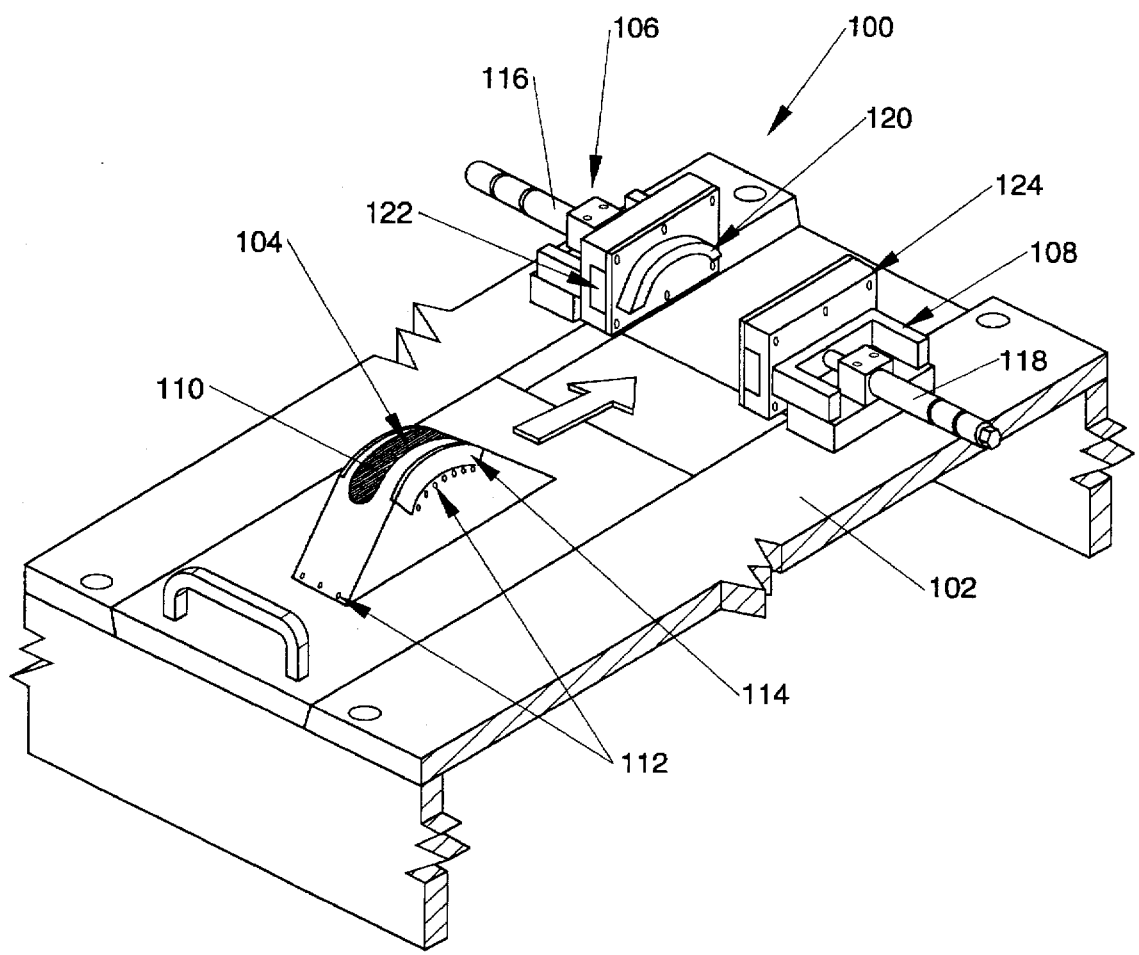
FIG. 16 is a perspective view of an apparatus that could be used to make the sanitary napkin of the present invention.
Figure 17:
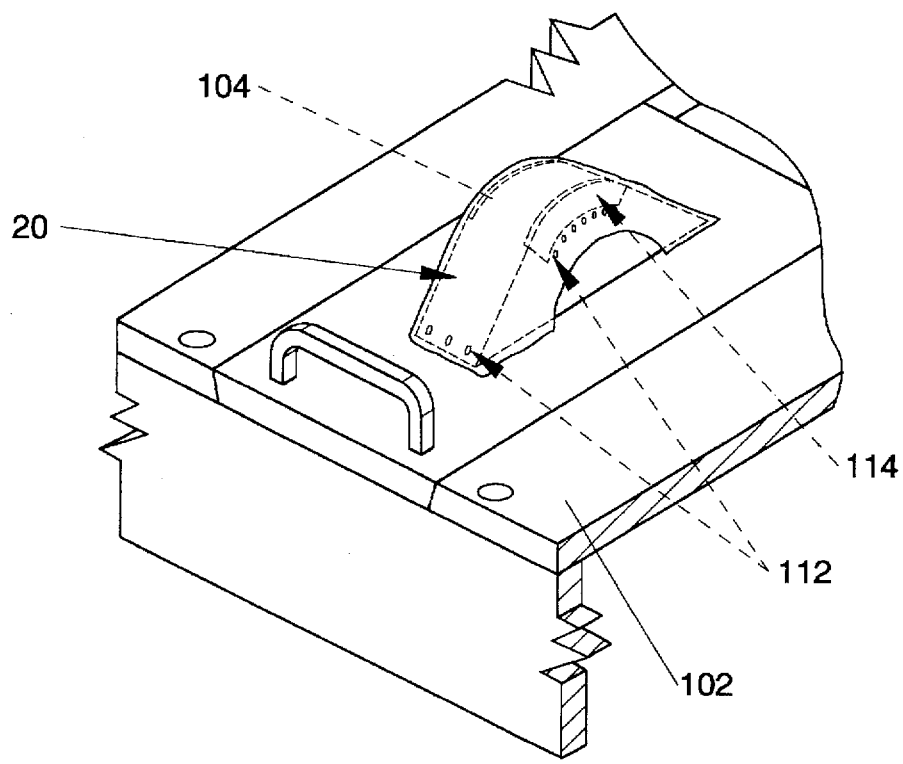
FIGS. 17 and 18 are close up views of a sanitary napkin being sealed on the apparatus shown in FIG. 16.
Figure 18:
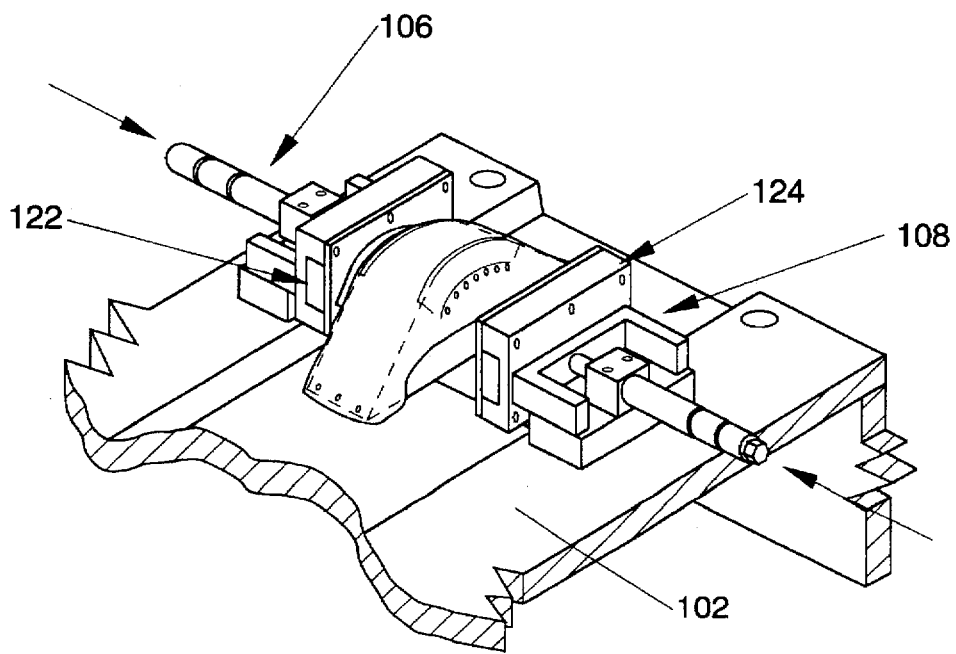

FIG. 16 shows an apparatus 100 that can be used to make the sanitary napkin of the present invention.

The apparatus 100 comprises the following basic components: a frame 102, a curved forming shoe 104 slidably mounted on the frame 102, and a pair of plungers 106 and 108. The components of the apparatus 100 are examined in greater detail below.

The curved forming shoe 104 serves as the curved form when the sanitary napkin is made on the apparatus 100. The curved forming shoe 104 is preferably provided with a recessed center portion 110, a plurality of vacuum holes 112, and a pair of silicone rubber inserts 114 on each side. A conventional vacuum source (not shown) is connected to the vacuum holes 112 on the curved forming shoe 104.

The untrimmed components of the sanitary napkin 20 are placed upside down on the curved forming shoe 104 (with the portions of the components that will form the hump 72 in the recessed center portion 110). The recessed center portion 110 provides a space for the center portion of the sanitary napkin provided with the capillary channel fiber bun to fit into when the sanitary napkin goes through the process of the present invention.

The vacuum holes 112 provide passageways for air to pass through when the vacuum is turned on. The vacuum source draws a vacuum through the vacuum holes 112. The vacuum is applied when the untrimmed sanitary napkin is placed on the curved forming shoe 104. The vacuum holds the untrimmed sanitary napkin in place during the sealing operation.

The curved forming shoe 104 slides with the untrimmed sanitary napkin thereon in the direction of the arrow in FIG. 16 between the plungers 106 and 108.

The plungers 106 and 108 preferably comprise pneumatic cylinders 116 and 118, heated sealing elements 120, strip heaters 122, and insulated element mounting blocks 124. The heated sealing elements 120 preferably have plasma coated faces that will come into contact with the sanitary napkin.

When the forming shoe 104 is between the plungers 106 and 108, the plungers are activated so that they move inward (in the cross machine direction) toward the forming shoe 104. The heated sealing elements 120 seal the longitudinal side margins 25 of the sanitary napkin with the silicone rubber inserts 114 serving as an anvil against which the force exerted by the plungers 106 and 108 is applied.

The subsequent steps of the assembly of the sanitary napkin, such as sealing the remainder of the perimeter of the sanitary napkin, and cutting the excess material outboard of the perimeter seal can be performed in any suitable manner.

C. Alternative Method—Foreshortening One or More Components of the Sanitary Napkin The second basic way of providing the sanitary napkin with curvature is by foreshortening one or more of the components of the sanitary napkin.

This method can be carried out in a number of ways. The preferred embodiment of this method involves constructing the sanitary napkin flat. One or more of the components (such as the topsheet 38) is stretched and secured to an underlying component or components (such as the backsheet 40). The stretched component is allowed to retract. This foreshortens the stretched component and generally causes the sanitary napkin to curve inward along the surface of the sanitary napkin that is nearest the foreshortened component.

(It is possible in other embodiments, however, that the sanitary napkin might curve inward along the surface that is farther away from the foreshortened component. The direction of curvature of the sanitary napkin depends on the characteristics of the other components of the sanitary napkin. For instance, if a soft, thick, and flexible material is placed on the outside surface of the foreshortened component, this could make the sanitary napkin curve inward along the surface that is farther away from the foreshortened component.)

For simplicity, the following description of this process will be described in terms of one preferred embodiment of the process in which the topsheet 38 comprises the component that is stretched and attached to the other components of the sanitary napkin.

The topsheet 38 material used in this process should have some elasticity. (That is, the topsheet material should be capable of extending and retracting.) The topsheet 38 material can comprise many of the materials described above. Preferably, the topsheet comprises one of the preferred formed films described above.

The permanent curvature and shape of the sanitary napkin is maintained as a result of the application of the topsheet 38 in a way such that there is less topsheet material (square area) than the dimensions of the backsheet 40. The pad curves upward to relieve the tension in the topsheet. The attachment of the stretched topsheet 38 to the other components can be thought of somewhat like the stringing of an archer's bow.

The topsheet 38 material preferably has relatively small amounts of extension and recovery properties. The topsheet 38 material should preferably not extend appreciably under the forces associated with wearing the sanitary napkin. This will ensure that the curvature is permanent throughout use. Otherwise (if the topsheet 38 was able to extend appreciably during wear), the extension of the topsheet 38 would cause the sanitary napkin 20 to flatten out and lose its curvature.

The topsheet 38 should have sufficient elastic recovery properties so that if the end regions 28 and 30 are pushed downward to flatten the sanitary napkin during wear, after the forces on the end regions are removed, the end regions will tend to spring back up to their original positions. As the product recovers its shape during use it helps bring the pad in contact with the body. It is also important that the topsheet material be soft and drapeable enough such that it maintains intimate contact with the underlying components throughout use as well.

The topsheet 38 material may be stretched uniformly along its length in the process of the present invention. That is, all portions of the topsheet 38 may be stretched the same amount.

Preferably, however, the topsheet 38 material is differentially stretched. The term "differentially stretched", as used herein, refers to a process in which some portions of a component (such as the topsheet) are stretched more than other portions of the component.

Figure 19:
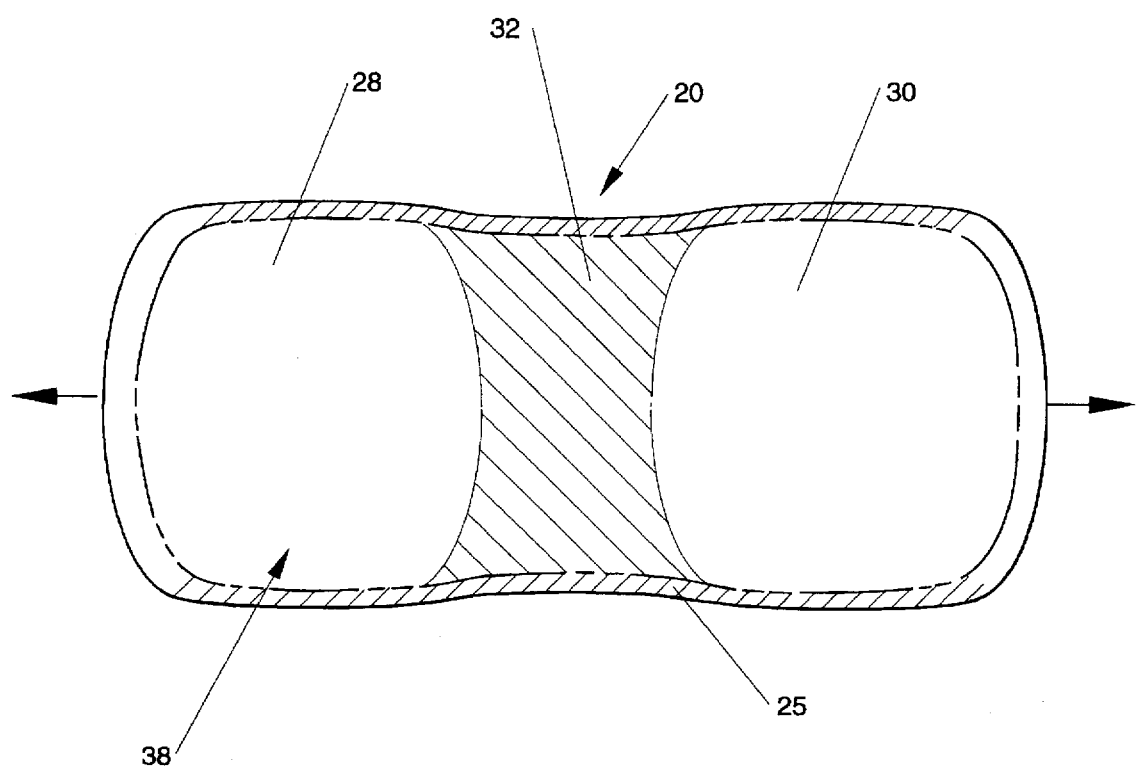
FIG. 19 is a plan view which shows the differential stretching of the topsheet that could be used to provide the sanitary napkin with curvature.

FIG. 19 shows that in a preferred process of making the sanitary napkin 20, the topsheet 38 is stretched longitudinally more in those portions that will lie in the central region 32 and in the longitudinal side regions 36 of the completely assembled sanitary napkin 20.

This is done prior to completely bonding the topsheet 38 to the backsheet 40. The differential stretching of the central region and the longitudinal side regions of the topsheet is achieved by first stretching the entire topsheet 38. The topsheet 38 is then secured to the backsheet 40 along the longitudinal side margins 25, but not elsewhere. After securing the longitudinal side margins of the topsheet 38 and backsheet 40, the topsheet 38 is allowed to relax. This removes the tension from the remaining portions of the topsheet 38. The topsheet 38 is then bonded to the backsheet 40 around the remainder of the perimeter of the sanitary napkin.

The advantage of selectively tensioning portions of the topsheet 38 is that it can be used to create preferred types of curvature. Stretching the portion of the topsheet 38 more in the central region 32 and the longitudinal side regions 36 of the sanitary napkin will produce greater curvature in these regions. This may be desirable to avoid making the end regions of the product tend to roll up. It also may be desirable for shaping the sanitary napkin to the configuration of the body for better product fit.

The topsheet 38 need only be stretched a relatively small amount of its unstretched length (for example, 1 or 2% to about 13%, or more preferably, 5–10% of its unstretched length) to impart curvature to the sanitary napkin 20. In other embodiments, it could be stretched more or less.

There are numerous alternative variations of all of the various processes of the present invention. These include, but are not limited to the following. All such alternatives are within the scope of the present invention.

The sanitary napkin could be provided with curvature by stretching other components of the sanitary napkin 20. The other components that can be stretched can also include, but are not limited to the secondary topsheet, and virtually any other component of the sanitary napkin. That is, provided that this other component or components are extensible and contractible. Thus, the capillary channel fiber bun 44 could not typically be stretched to provide the sanitary napkin with curvature.

To provide the desired direction of curvature, the z-direction location of the stretched component, as well as characteristics, such as the flexibility of the adjacent components must be taken into consideration in choosing the component to be stretched.

The stretched component(s) of the sanitary napkin may be joined to the backsheet 40 at their perimeters as described above. In alternative embodiments, the stretched component(s) can be joined to some component or components other than the backsheet 40. The only requirement for such other component(s) is that it be stretched less than the stretched component.

Further, the components may be joined together at locations other than their perimeters and still provide the sanitary napkin 20 with curvature. The components will typically have to be joined at at least two places to impart curvature to the sanitary napkin. These two places should be selected so that they are located at places other than at the intersection of the longitudinal and transverse centerlines.

In alternative embodiments, the component of the sanitary napkin that is stretched does not have to comprise a layer (or portion of a layer) that extends the full dimensions of the sanitary napkin to nearly the full dimensions of the sanitary napkin. For example, the component that is stretched need comprise only a strip of material that is stretched and secured which provides the sanitary napkin with curvature. Preferably, conventional elastic strands are not used solely for this purpose for the reasons discussed above.

The processes described above could be used to provide the sanitary napkin with lateral curvature. This lateral curvature could be instead of, or in addition to, the longitudinal curvature provided by the process described above.

In other embodiments, some of the techniques described in P&G U.K. Patent Application 2 168 253A published in the name of Baird, et al. on Jun. 16, 1986 and in U.S. patent application Ser. No. 07/882,738 filed in the name of Taylor, et al. on May 14, 1992 could be used in the construction of the sanitary napkin.

Elastic members (used in some sanitary pads to provide 3-D shaping) may not be comfortable or perceived as comfortable by consumers as well as creating gaps between the sanitary pad and the wearer's body which can provide opportunities for menses fluid leakage. In addition to the consumer drawbacks of separate elastic members, these materials add cost and complexity to manufacturing these types of pads.

By using the elastomeric properties of one of the components of the absorbent article, almost any absorbent article which is made today can be made using this technique. It is believed that this technique will result in a smooth, curved absorbent article which ideally fits the wearer's body more closely and more comfortably than flat absorbent articles or absorbent articles that rely on elastic members to create curvature. Absorbent articles that fit the wearer's body closely and comfortably provide better protection from soiling.

In other embodiments, however, the stretching could be used to create rugosities in the sanitary napkin, if desired. These rugosities could be created instead of, or in addition to curvature.

In still other embodiments (or all the processes described herein), the sanitary napkin 20 could also be provided with optional elastics. These elastics could be applied in any manner known in the art.

D. Alternative Method—Lengthening One of More Components of the Sanitary Napkin

The third way, noted above, of the curving the sanitary napkin 20 is by some suitable process which results in lengthening one of the faces of the sanitary napkin 20.

This can, for example, be done by stretching the backsheet 40 of the sanitary napkin 20, or by heating and stretching the backsheet 40.

The stretching in such a process could be carried out on a flat pre-assembled sanitary napkin that is bonded at places other than the longitudinal side margins. The pre-assembled sanitary napkin could be placed in or against a curved form. The backsheet 40 can be stretched for the pre-assembled sanitary napkin to assume the configuration of the curved form. The longitudinal side margins (or some other suitable portions) of the pre-assembled sanitary napkin are then sealed while the pre-assembled sanitary napkin is in a curved configuration. This will result in a sanitary napkin that is curved inward along the topsheet 38.

In alternative embodiments, some component or components other than the backsheet (or in addition to the backsheet 40) could be extended.

The general principles discussed above relating to alternative variations of the above processes such as foreshortening components of the sanitary napkin to create curvature (e.g., using the technique to create cross direction curvature) can also be applied to alternative processes that use lengthening of components to create curvature.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention.

It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a main body portion having longitudinal sides and transverse ends, a body-facing surface and a garment-facing surface, said article comprising:

a liquid pervious topsheet on said body-facing surface;

a liquid impervious backsheet on said garment-facing surface joined to said to said topsheet;

an absorbent core positioned between said liquid pervious topsheet and said liquid impervious backsheet, said absorbent core having a central portion located inward of said transverse ends and a center said raised center having a pair of transverse end portions;

said absorbent core further comprising at least one bending axis located longitudinally outboard of the transverse end portions of the raised center, at least a portion of said absorbent core comprising a material arranged in a structure that is resistant to wet collapse; and a pair of flaps joined to said main body portion and extending outward along each longitudinal side thereof;

wherein said absorbent article preferentially bends at said bending axis.

2. The absorbent article of claim 1 wherein there are two bending axes located longitudinally outboard of the transverse end portions of the raised center.

3. The absorbent article of claim 1 wherein said portion of said absorbent core that is resilient when wet is more resilient than other portions of said absorbent core.

4. The absorbent article of claim 1 wherein said absorbent core at least partially comprises peat moss.

5. An absorbent article having longitudinal sides and transverse ends, a body-facing surface, and a garment-facing surface, said absorbent article comprising:

a liquid pervious topsheet on said body-facing surface;

an absorbent core adjacent said liquid pervious topsheet, said absorbent core having a central portion located inward of said transverse ends and a raised center comprising a material arranged in a structure that is resistant to wet collapse, said raised center having a pair of transverse end portions;

said absorbent core further comprising at least one transversely oriented bending axis located longitudinally outboard of the transverse end portions of the raised center; and a liquid impervious backsheet on said garment-facing surface joined to said topsheet;

wherein said absorbent article preferentially bends at said bending axis.

6. The absorbent article of claim 5 wherein the absorbent core contains a transfer layer and a reservoir layer.

7. The absorbent article of claim 5 wherein said absorbent core at least partially comprises peat moss.

8. The absorbent article of claim 5 wherein there are two bending axes located longitudinally outboard of the transverse end portions of the raised center.

9. The absorbent article of claim 8 wherein the central portion of the absorbent core has a structural zone which is located between the bending axes.

10. The absorbent article of claim 8 wherein the absorbent article further contains flaps.

11. The absorbent article of claim 10 wherein the flaps are affixed to the absorbent article at positions between each bending axis.

* * * * *